United States Patent
Xie et al.

(10) Patent No.: US 11,667,896 B2
(45) Date of Patent: Jun. 6, 2023

(54) MODIFIED DAAO ENZYME AND APPLICATION THEREOF

(71) Applicant: HUNAN LIER BIOTECH CO., LTD., Hunan (CN)

(72) Inventors: Xinkai Xie, Jiangsu (CN); Wei Xu, Jiangsu (CN); Junying Fan, Jiangsu (CN)

(73) Assignee: Hunan Lier Biotech Co., LTD, Hunan (CN)

( * ) Notice: Subject to any disclaimer, the term of this patent is extended or adjusted under 35 U.S.C. 154(b) by 0 days.

(21) Appl. No.: 17/836,773

(22) Filed: Jun. 9, 2022

(65) Prior Publication Data
US 2022/0333086 A1    Oct. 20, 2022

Related U.S. Application Data

(63) Continuation of application No. PCT/CN2020/134540, filed on Dec. 8, 2020.

(30) Foreign Application Priority Data

Dec. 9, 2019  (CN) .......................... 201911249924.4

(51) Int. Cl.
*C12N 15/52* (2006.01)
*C12N 9/02* (2006.01)
*C12P 41/00* (2006.01)

(52) U.S. Cl.
CPC ............ *C12N 9/0004* (2013.01); *C12P 41/00* (2013.01); *C12N 2320/50* (2013.01); *C12N 2330/50* (2013.01)

(58) Field of Classification Search
CPC .......... C12N 15/52; C12N 15/09; C12N 9/10; C12Y 121/00; C12P 5/00
IPC ..................................................... C12N 15/52
See application file for complete search history.

(56) References Cited

U.S. PATENT DOCUMENTS

2019/0185889 A1   6/2019  Green et al.
2022/0010342 A1*  1/2022  Tian ........................ C12P 9/00

FOREIGN PATENT DOCUMENTS

| CN | 1639344 A | 7/2005 |
| CN | 109072261 A | 12/2018 |
| CN | 109576236 A | 4/2019 |
| CN | 111019916 A | 4/2020 |
| WO | WO 2020051188 A1 | 3/2020 |

OTHER PUBLICATIONS

Hawkes. T. et al. "D-glufosinate as a Male Sterility Agent for Hybrid Seed Production" Plant Biotechnology Journal, vol. 9, No. 3, Apr. 30, 2011 (Apr. 30, 2011), 301-314.

Sacchi, S. et al. "Engineering the Substrate Specificity of D-Amino-acid Oxidase" The Journal of Biological Chemistry, vol. 277, No. 30, Jul. 26, 2002 (Jul. 26, 2002), 27510-27516.

Boselli A. et al. "Investigating the Role of Active Site Residues of Rhodotorula Gracilis D-Amino Acid Oxidase on Its Substrate Specificity" Biochimie, vol. 89, Nov. 27, 2006 (Nov. 27, 2006), 360-368.

Zhao, Ranran et al.). "D—(Research Progress on the Crystal Structure of D-amino Acid Oxidase)" (Biotechnology Bulletin), No. 12, Dec. 25, 2013 (Dec. 25, 2013), 27-35.

Pollegioni et al., "Human D-Amino Acid Oxidase: Structure, Function, and Regulation", vol. 5, Frontiers in Molecular Biosciences, Nov. 28, 2018, pp. 1-14.

* cited by examiner

*Primary Examiner* — Tekchand Saidha
(74) *Attorney, Agent, or Firm* — Stites & Harbison PLLC; Richard S. Myers, Jr.

(57) ABSTRACT

The present invention refers to a modified D-amino acid oxidase (DAAO). In particular, the modified DAAO of the present invention has the activity of catalyzing the oxidation of D-glufosinate into PPO. Further, the modified DAAO of the present invention has increased activity of catalyzing the oxidation of D-glufosinate into PPO and/or increased stability as compared to SEQ ID NO: 4. The present invention also refers to the polynucleotide encoding the modified DAAO of the present invention, the vector and host cell expressing the modified DAAO of the present invention, and the method of producing L-glufosinate with the modified DAAO and host cell of the present invention.

11 Claims, No Drawings

Specification includes a Sequence Listing.

SEQUENCE LISTING

```
<160> NUMBER OF SEQ ID NOS: 86

<210> SEQ ID NO 1
<211> LENGTH: 368
<212> TYPE: PRT
<213> ORGANISM: Rhodotorula gracilis

<400> SEQUENCE: 1

Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
                35                  40                  45

Pro Trp Ala Gly Ala Asn Trp Thr Pro Phe Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
                100                 105                 110
```

```
Pro Asn Tyr Arg Pro Leu Pro Ser Glu Cys Pro Pro Gly Ala Ile
            115                 120                 125

Gly Val Thr Tyr Asp Thr Leu Ser Val His Ala Pro Lys Tyr Cys Gln
130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Arg Cys Thr Met Asp Ser Ser Asp Pro Ala Ser Pro Ala Tyr Ile
210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365
```

<210> SEQ ID NO 2
<211> LENGTH: 372
<212> TYPE: PRT
<213> ORGANISM: Rhodotorula sp. JG-1b

<400> SEQUENCE: 2

```
Met Thr Gln Asn Lys Arg Val Val Leu Gly Ser Gly Val Ile Gly
1                   5                   10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
            35                  40                  45

Pro Trp Ala Gly Ala Asn Trp Thr Pro Phe Met Ser Lys Glu Ala Gly
        50                  55                  60

Pro Arg Gln Ala Lys Trp Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125
```

-continued

Gly Val Thr Tyr Asp Thr Leu Ser Val Asn Ala Pro Lys Phe Cys Gln
            130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
            195                 200                 205

Lys Arg Cys Thr Met Asp Ser Ser Asp Pro Lys Ser Pro Ala Tyr Ile
            210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
            275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
            355                 360                 365

Leu Ala Lys Leu
    370

<210> SEQ ID NO 3
<211> LENGTH: 372
<212> TYPE: PRT
<213> ORGANISM: Rhodotorula taiwanensis

<400> SEQUENCE: 3

Met Ala Pro Ser Lys Arg Val Val Leu Gly Ser Gly Val Val Gly
1               5                   10                  15

Leu Ser Ser Ala Leu Thr Leu Ala Gln Lys Gly Tyr Ser Val His Val
                20                  25                  30

Val Ala Arg Asp Leu Pro Glu Asp Thr Val Ala Gln Thr Phe Ala Ser
            35                  40                  45

Pro Trp Ala Gly Ala Asn Trp Thr Pro Phe Met Ser Lys Glu Asp Gly
        50                  55                  60

Pro Arg Gln Ala Lys Trp Glu Thr Ala Thr Phe Asn Gln Trp Val Asp
65                  70                  75                  80

Leu Val Pro Gln Gly Leu Ala Met Trp Leu Lys Gly Thr Arg Arg Tyr
                85                  90                  95

Ala Gln Asp Glu Ala Gly Leu Leu Gly His Trp Tyr Gln His Ile Thr
            100                 105                 110

Pro Asn Tyr Arg Lys Leu Glu Ser Ser Glu Cys Pro Pro Gly Ala Ile

```
                115                 120                 125
Gly Val Thr Tyr Asp Thr Leu Ser Val Asn Ala Pro Lys Phe Cys Gln
            130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Glu Gly Phe Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Val Lys Ser Asp Cys
            195                 200                 205

Lys Arg Cys Thr Met Asp Ser Ser Asp Pro Asn Ser Pro Ala Tyr Ile
            210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Pro Thr Ile Asn Arg Ile Leu
                245                 250                 255

Gln His Cys Leu Arg Leu Asp Pro Ser Ile Ser Thr Asp Gly Thr Leu
            260                 265                 270

Glu Gly Ile Glu Ile Val Arg His Asn Val Gly Leu Arg Pro Ala Arg
            275                 280                 285

Arg Gly Gly Pro Arg Val Glu Val Glu Arg Val Ala Phe Pro Leu Glu
290                 295                 300

Arg Gly Lys Ser Lys Leu Ser Leu Gly Thr Ala Arg Ala Asp Ser Ser
305                 310                 315                 320

Lys Pro Arg Arg Glu Val Pro Val Val His Ala Tyr Gly Phe Ser Ser
                325                 330                 335

Ala Gly Tyr Gln Gln Gly Trp Gly Ala Ala Leu Glu Val Ala Glu Leu
            340                 345                 350

Val Glu Gly Ala Ile Gly Ala Ala Pro Ala Arg Ser Ser His Arg Trp
            355                 360                 365

Leu Ser Lys Leu
    370

<210> SEQ ID NO 4
<211> LENGTH: 368
<212> TYPE: PRT
<213> ORGANISM: Artificial Sequence
<220> FEATURE:
<223> OTHER INFORMATION: mutant DAAO

<400> SEQUENCE: 4

Met Gly Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Val Trp Thr Pro Gln Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

-continued

```
                100                 105                 110
Pro Asn Tyr Arg Pro Leu Pro Ser Ser Glu Cys Pro Pro Gly Ala Ile
            115                 120                 125
Gly Val Thr Tyr Asp Thr Leu Ser Val His Ala Pro Lys Tyr Cys Gln
        130                 135                 140
Tyr Leu Ala Arg Glu Leu Gln Lys Leu Gly Ala Thr Phe Glu Arg Arg
145                 150                 155                 160
Thr Val Thr Ser Leu Glu Gln Ala Phe Asp Gly Ala Asp Leu Val Val
                165                 170                 175
Asn Ala Thr Gly Leu Gly Ala Lys Ser Ile Ala Gly Ile Asp Asp Gln
            180                 185                 190
Ala Ala Glu Pro Ile Arg Gly Gln Thr Val Leu Val Lys Ser Pro Cys
        195                 200                 205
Lys Arg Cys Thr Ser Asp Ser Ser Asp Pro Ala Ser Pro Ala Tyr Ile
    210                 215                 220
Ile Pro Arg Pro Gly Gly Glu Val Ile Cys Gly Gly Thr Tyr Gly Val
225                 230                 235                 240
Gly Asp Trp Asp Leu Ser Val Asn Pro Glu Thr Val Gln Arg Ile Leu
                245                 250                 255
Lys His Cys Leu Arg Leu Asp Pro Thr Ile Ser Ser Asp Gly Thr Ile
            260                 265                 270
Glu Gly Ile Glu Val Leu Arg His Asn Val Gly Leu Arg Pro Ala Arg
        275                 280                 285
Arg Gly Gly Pro Arg Val Glu Ala Glu Arg Ile Val Leu Pro Leu Asp
    290                 295                 300
Arg Thr Lys Ser Pro Leu Ser Leu Gly Arg Gly Ser Ala Arg Ala Ala
305                 310                 315                 320
Lys Glu Lys Glu Val Thr Leu Val His Ala Tyr Gly Phe Ser Ser Ala
                325                 330                 335
Gly Tyr Gln Gln Ser Trp Gly Ala Ala Glu Asp Val Ala Gln Leu Val
            340                 345                 350
Asp Glu Ala Phe Gln Arg Tyr His Gly Ala Ala Arg Glu Ser Lys Leu
        355                 360                 365

<210> SEQ ID NO 5
<211> LENGTH: 368
<212> TYPE: PRT
<213> ORGANISM: Artificial Sequence
<220> FEATURE:
<223> OTHER INFORMATION: mutant DAAO

<400> SEQUENCE: 5

Met Gly Ser Gln Lys Arg Val Val Val Leu Gly Ser Gly Val Ile Gly
1               5                   10                  15
Leu Ser Ser Ala Leu Ile Leu Ala Arg Lys Gly Tyr Ser Val His Ile
            20                  25                  30
Leu Ala Arg Asp Leu Pro Glu Asp Val Ser Ser Gln Thr Phe Ala Ser
        35                  40                  45
Pro Trp Ala Gly Ala Val Trp Thr Pro Gln Met Thr Leu Thr Asp Gly
    50                  55                  60
Pro Arg Gln Ala Lys Trp Glu Glu Ser Thr Phe Lys Lys Trp Val Glu
65                  70                  75                  80
Leu Val Pro Thr Gly His Ala Met Trp Leu Lys Gly Thr Arg Arg Phe
                85                  90                  95
Ala Gln Asn Glu Asp Gly Leu Leu Gly His Trp Tyr Lys Asp Ile Thr
```

```
            100                 105                 110
Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
                180                 185                 190

Ala Val Glu Pro Ile Arg Gly Gln Thr Val Leu Val Lys Ser Pro Cys
                195                 200                 205

Lys Arg Cys Thr Ser Asp Ser Ser Asp Pro Ala Ser Pro Ala Tyr Ile
                210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
                260                 265                 270

Glu Gly Ile Glu Val Leu Arg His Asn Val Gly Leu Arg Pro Ala Arg
                275                 280                 285

Arg Gly Gly Pro Arg Val Glu Ala Glu Arg Ile Val Leu Pro Leu Asp
                290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
                340                 345                 350

Asp Glu Ala Phe Gln Arg Tyr His Gly Ala Ala Arg Glu Ser Lys Leu
                355                 360                 365

<210> SEQ ID NO 6
<211> LENGTH: 368
<212> TYPE: PRT
<213> ORGANISM: Artificial Sequence
<220> FEATURE:
<223> OTHER INFORMATION: mutant DAAO

<400> SEQUENCE: 6

Met Gly Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
                35                  40                  45

Pro Trp Ala Gly Ala Val Trp Thr Pro Gln Met Thr Leu Thr Asp Gly
                50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
            100                 105                 110
Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
        130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Cys Glu Pro Ile Arg Gly Gln Thr Val Leu Val Lys Ser Pro Cys
        195                 200                 205

Lys Arg Cys Thr Ser Asp Ser Ser Asp Pro Ala Ser Pro Ala Tyr Ile
        210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
        290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365

<210> SEQ ID NO 7
<211> LENGTH: 368
<212> TYPE: PRT
<213> ORGANISM: Artificial Sequence
<220> FEATURE:
<223> OTHER INFORMATION: mutant DAAO

<400> SEQUENCE: 7

Met Gly Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Val Trp Thr Pro Gln Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
            100                 105                 110
Pro Asn Tyr Arg Pro Leu Pro Ser Ser Glu Cys Pro Pro Gly Ala Ile
            115                 120                 125

Gly Val Thr Tyr Asp Thr Leu Ser Val His Ala Pro Lys Tyr Cys Gln
            130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                    165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
            195                 200                 205

Lys Arg Cys Thr Ser Asp Ser Ser Asp Pro Ala Ser Pro Ala Tyr Ile
            210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                    245                 250                 255

Lys His Cys Leu Arg Leu Asp Pro Thr Ile Ser Ser Asp Gly Thr Ile
            260                 265                 270

Asp Gly Ile Glu Val Leu Arg His Asn Val Gly Leu Arg Pro Ala Arg
            275                 280                 285

Arg Gly Gly Pro Arg Val Glu Ala Glu Arg Ile Val Leu Pro Leu Asp
            290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                    325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
            355                 360                 365

<210> SEQ ID NO 8
<211> LENGTH: 368
<212> TYPE: PRT
<213> ORGANISM: Artificial Sequence
<220> FEATURE:
<223> OTHER INFORMATION: mutant DAAO

<400> SEQUENCE: 8

Met Gly Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
            35                  40                  45

Pro Trp Ala Gly Ala Val Trp Thr Pro Gln Met Thr Leu Thr Asp Gly
            50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                    85                  90                  95

Ala Gln Asn Glu Asp Gly Leu Leu Gly His Trp Tyr Lys Asp Ile Thr
```

```
                100             105                 110
       Pro Asn Tyr Arg Pro Leu Pro Ser Ser Glu Cys Pro Pro Gly Ala Ile
                    115                 120                 125
       Gly Val Thr Tyr Asp Thr Leu Ser Val His Ala Pro Lys Tyr Cys Gln
                    130                 135             140
       Tyr Leu Ala Arg Glu Leu Gln Lys Leu Gly Ala Thr Phe Glu Arg Arg
       145                 150                 155                 160
       Thr Val Thr Ser Leu Glu Gln Ala Phe Asp Gly Ala Asp Leu Val Val
                        165                 170                 175
       Asn Ala Thr Gly Leu Gly Ala Lys Ser Ile Ala Gly Ile Asp Asp Gln
                    180                 185                 190
       Ala Ala Glu Pro Ile Arg Gly Gln Thr Val Leu Val Lys Ser Pro Cys
                    195                 200                 205
       Lys Arg Cys Thr Ser Asp Ser Ser Asp Pro Ala Ser Pro Ala Tyr Ile
                    210                 215                 220
       Ile Pro Arg Pro Gly Gly Glu Val Ile Cys Gly Gly Thr Tyr Gly Val
       225                 230                 235                 240
       Gly Asp Trp Asp Leu Ser Val Asn Pro Glu Thr Val Gln Arg Ile Leu
                        245                 250                 255
       Lys His Cys Leu Arg Leu Asp Pro Thr Ile Ser Ser Asp Gly Thr Ile
                    260                 265                 270
       Glu Gly Ile Glu Val Leu Arg His Asn Val Gly Leu Arg Pro Ala Arg
                    275                 280                 285
       Arg Gly Gly Pro Arg Val Glu Ala Glu Arg Ile Val Leu Pro Leu Asp
                    290                 295                 300
       Arg Thr Lys Ser Pro Leu Ser Leu Gly Arg Gly Ser Tyr Arg Ala Ala
       305                 310                 315                 320
       Lys Glu Lys Glu Val Thr Leu Val His Ala Tyr Gly Phe Ser Ser Ala
                        325                 330                 335
       Gly Tyr Gln Gln Ser Trp Gly Ala Ala Glu Asp Val Ala Gln Leu Val
                    340                 345                 350
       Asp Glu Ala Phe Gln Arg Tyr His Gly Ala Ala Arg Glu Ser Lys Leu
                    355                 360                 365

<210> SEQ ID NO 9
<211> LENGTH: 368
<212> TYPE: PRT
<213> ORGANISM: Artificial Sequence
<220> FEATURE:
<223> OTHER INFORMATION: mutant DAAO

<400> SEQUENCE: 9

Met Gly Ser Gln Lys Arg Val Val Leu Gly Ser Gly Val Ile Gly
       1               5                   10                  15
       Leu Ser Ser Ala Leu Ile Leu Ala Arg Lys Gly Tyr Ser Val His Ile
                        20                  25                  30
       Leu Ala Arg Asp Leu Pro Glu Asp Val Ser Ser Gln Thr Phe Ala Ser
                    35                  40                  45
       Pro Trp Ala Gly Ala Val Trp Thr Pro Gln Met Thr Leu Thr Asp Gly
                50                  55                  60
       Pro Arg Gln Ala Lys Trp Glu Glu Ser Thr Phe Lys Lys Trp Val Glu
       65                  70                  75                  80
       Leu Val Pro Thr Gly His Ala Met Trp Leu Lys Gly Thr Arg Arg Phe
                        85                  90                  95
       Ala Gln Asn Glu Asp Gly Leu Leu Gly His Trp Tyr Lys Asp Ile Thr
```

```
                    100                 105                 110
Pro Asn Tyr Arg Pro Leu Pro Ser Ser Glu Cys Pro Pro Gly Ala Ile
            115                 120                 125

Gly Val Thr Tyr Asp Thr Leu Ser Val His Ala Pro Lys Tyr Cys Gln
            130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
            195                 200                 205

Lys Arg Cys Thr Ser Asp Ser Ser Asp Pro Ala Ser Pro Ala Tyr Ile
            210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
            275                 280                 285

Arg Gly Gly Pro Arg Val Glu Ala Glu Arg Ile Val Leu Pro Leu Asp
            290                 295                 300

Arg Thr Lys Ser Pro Leu Ser Leu Gly Arg Gly Ser Trp Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
            355                 360                 365

<210> SEQ ID NO 10
<211> LENGTH: 368
<212> TYPE: PRT
<213> ORGANISM: Artificial Sequence
<220> FEATURE:
<223> OTHER INFORMATION: mutant DAAO

<400> SEQUENCE: 10

Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
            35                  40                  45

Pro Trp Ala Gly Ala Val Trp Thr Pro Gln Met Thr Leu Thr Asp Gly
            50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
            100                 105                 110
Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
        130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Arg Cys Thr Ser Asp Ser Ser Asp Pro Ala Ser Pro Ala Tyr Ile
        210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Glu Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
        290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365

<210> SEQ ID NO 11
<211> LENGTH: 368
<212> TYPE: PRT
<213> ORGANISM: Artificial Sequence
<220> FEATURE:
<223> OTHER INFORMATION: mutant DAAO

<400> SEQUENCE: 11

Met Gly Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Val Trp Thr Pro Gln Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
            100                 105                 110
Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Arg Cys Thr Ser Asp Ser Ser Asp Pro Ala Ser Pro Ala Tyr Ile
    210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
    290                 295                 300

Arg Thr Lys Ser Pro Leu Ser Leu Gly Arg Gly Ser Ala Arg Lys Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365

<210> SEQ ID NO 12
<211> LENGTH: 368
<212> TYPE: PRT
<213> ORGANISM: Artificial Sequence
<220> FEATURE:
<223> OTHER INFORMATION: mutant DAAO

<400> SEQUENCE: 12

Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
            35                  40                  45

Pro Trp Ala Gly Ala Val Trp Thr Pro Gln Met Thr Leu Thr Asp Gly
        50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
            100                 105                 110
Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
        130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Cys Glu Pro Ile Arg Gly Gln Thr Val Leu Val Lys Ser Pro Cys
        195                 200                 205

Lys Arg Cys Thr Ser Asp Ser Ser Asp Pro Ala Ser Pro Ala Tyr Ile
        210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
290                 295                 300

Arg Thr Lys Ser Pro Leu Ser Leu Gly Arg Gly Ser Tyr Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365

<210> SEQ ID NO 13
<211> LENGTH: 368
<212> TYPE: PRT
<213> ORGANISM: Artificial Sequence
<220> FEATURE:
<223> OTHER INFORMATION: mutant DAAO

<400> SEQUENCE: 13

Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Val Trp Thr Pro Gln Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
            100                 105                 110
Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Cys Glu Pro Ile Arg Gly Gln Thr Val Leu Val Lys Ser Pro Cys
        195                 200                 205

Lys Arg Cys Thr Ser Asp Ser Ser Asp Pro Ala Ser Pro Ala Tyr Ile
    210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Cys Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
    290                 295                 300

Arg Thr Lys Ser Pro Leu Ser Leu Gly Arg Gly Ser Tyr Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365

<210> SEQ ID NO 14
<211> LENGTH: 368
<212> TYPE: PRT
<213> ORGANISM: Artificial Sequence
<220> FEATURE:
<223> OTHER INFORMATION: mutant DAAO

<400> SEQUENCE: 14

Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
            35                  40                  45

Pro Trp Ala Gly Ala Val Trp Thr Pro Gln Met Thr Leu Thr Asp Gly
        50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
            100                 105                 110
Pro Asn Tyr Arg Pro Leu Pro Ser Ser Glu Cys Pro Gly Ala Ile
        115                 120                 125

Gly Val Thr Tyr Asp Thr Leu Ser Val His Ala Pro Lys Tyr Cys Gln
        130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
                180                 185                 190

Ala Cys Glu Pro Ile Arg Gly Gln Thr Val Leu Val Lys Ser Pro Cys
                195                 200                 205

Lys Arg Cys Thr Ser Asp Ser Ser Asp Pro Ala Ser Pro Ala Tyr Ile
                210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Cys Ile Ser Ser Asp Gly Thr Ile
                260                 265                 270

Glu Gly Ile Glu Val Leu Arg His Asn Val Gly Leu Arg Pro Ala Arg
                275                 280                 285

Arg Gly Gly Pro Arg Val Glu Ala Glu Arg Ile Ser Leu Pro Leu Asp
                290                 295                 300

Arg Thr Lys Ser Pro Leu Ser Leu Gly Arg Gly Ser Tyr Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
                340                 345                 350

Asp Glu Ala Phe Gln Arg Tyr His Gly Ala Ala Arg Glu Ser Lys Leu
                355                 360                 365

<210> SEQ ID NO 15
<211> LENGTH: 368
<212> TYPE: PRT
<213> ORGANISM: Artificial Sequence
<220> FEATURE:
<223> OTHER INFORMATION: mutant DAAO

<400> SEQUENCE: 15

Met Gly Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
                35                  40                  45

Pro Trp Ala Gly Ala Val Trp Thr Pro Gln Met Thr Leu Thr Asp Gly
        50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
            100                 105                 110
Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
        130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Cys Glu Pro Ile Arg Gly Gln Thr Val Leu Val Lys Ser Pro Cys
        195                 200                 205

Lys Arg Cys Thr Thr Asp Ser Ser Asp Pro Ala Ser Pro Ala Tyr Ile
        210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Cys Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Ser Leu Pro Leu Asp
        290                 295                 300

Arg Thr Lys Ser Pro Leu Ser Leu Gly Arg Gly Ser Tyr Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365

<210> SEQ ID NO 16
<211> LENGTH: 368
<212> TYPE: PRT
<213> ORGANISM: Artificial Sequence
<220> FEATURE:
<223> OTHER INFORMATION: mutant DAAO

<400> SEQUENCE: 16

Met Gly Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Val Trp Thr Pro Gln Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
            100                 105                 110
Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
        130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
                180                 185                 190

Ala Cys Glu Pro Ile Arg Gly Gln Thr Val Leu Val Lys Ser Pro Cys
            195                 200                 205

Lys Gly Cys Thr Ser Asp Ser Asp Pro Ala Ser Pro Ala Tyr Ile
        210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Cys Ile Ser Ser Asp Gly Thr Ile
                260                 265                 270

Glu Gly Ile Glu Val Leu Arg His Asn Val Gly Leu Arg Pro Ala Arg
            275                 280                 285

Arg Gly Gly Pro Arg Val Glu Ala Glu Arg Ile Ser Leu Pro Leu Asp
        290                 295                 300

Arg Thr Lys Ser Pro Leu Ser Leu Gly Arg Gly Ser Tyr Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
                340                 345                 350

Asp Glu Ala Phe Gln Arg Tyr His Gly Ala Ala Arg Glu Ser Lys Leu
        355                 360                 365

<210> SEQ ID NO 17
<211> LENGTH: 368
<212> TYPE: PRT
<213> ORGANISM: Artificial Sequence
<220> FEATURE:
<223> OTHER INFORMATION: mutant DAAO

<400> SEQUENCE: 17

Met Gly Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
            35                  40                  45

Pro Trp Ala Gly Ala Val Trp Thr Pro Gln Met Thr Leu Thr Asp Gly
        50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
            100                 105                 110
Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Cys Glu Pro Ile Arg Gly Gln Thr Val Leu Val Lys Ser Pro Cys
        195                 200                 205

Lys Pro Cys Thr Ser Asp Ser Ser Asp Pro Ala Ser Pro Ala Tyr Ile
    210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Cys Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Ser Leu Pro Leu Asp
    290                 295                 300

Arg Thr Lys Ser Pro Leu Ser Leu Gly Arg Gly Ser Tyr Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365

<210> SEQ ID NO 18
<211> LENGTH: 368
<212> TYPE: PRT
<213> ORGANISM: Artificial Sequence
<220> FEATURE:
<223> OTHER INFORMATION: mutant DAAO

<400> SEQUENCE: 18

Met Gly Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Val Trp Thr Pro Gln Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

-continued

```
                100             105                 110
    Pro Asn Tyr Arg Pro Leu Pro Ser Ser Glu Cys Pro Gly Ala Ile
            115                 120                 125
    Gly Val Thr Tyr Asp Thr Leu Ser Val His Ala Pro Lys Tyr Cys Gln
    130                 135                 140
    Tyr Leu Ala Arg Glu Leu Gln Lys Leu Gly Ala Thr Phe Glu Arg Arg
    145                 150                 155                 160
    Thr Val Thr Ser Leu Glu Gln Ala Phe Asp Gly Ala Asp Leu Val Val
                165                 170                 175
    Asn Ala Thr Gly Leu Gly Ala Lys Ser Ile Ala Gly Ile Asp Asp Gln
                180                 185                 190
    Ala Cys Glu Pro Ile Arg Gly Gln Thr Val Leu Val Lys Ser Pro Cys
                195                 200                 205
    Lys Ala Cys Thr Ser Asp Ser Ser Asp Pro Ala Ser Pro Ala Tyr Ile
    210                 215                 220
    Ile Pro Arg Pro Gly Gly Glu Val Ile Cys Gly Gly Thr Tyr Gly Val
    225                 230                 235                 240
    Gly Asp Trp Asp Leu Ser Val Asn Pro Glu Thr Val Gln Arg Ile Leu
                245                 250                 255
    Lys His Cys Leu Arg Leu Asp Pro Cys Ile Ser Ser Asp Gly Thr Ile
                260                 265                 270
    Glu Gly Ile Glu Val Leu Arg His Asn Val Gly Leu Arg Pro Ala Arg
                275                 280                 285
    Arg Gly Gly Pro Arg Val Glu Ala Glu Arg Ile Ser Leu Pro Leu Asp
    290                 295                 300
    Arg Thr Lys Ser Pro Leu Ser Leu Gly Arg Gly Ser Tyr Arg Ala Ala
    305                 310                 315                 320
    Lys Glu Lys Glu Val Thr Leu Val His Ala Tyr Gly Phe Ser Ser Ala
                325                 330                 335
    Gly Tyr Gln Gln Ser Trp Gly Ala Ala Glu Asp Val Ala Gln Leu Val
                340                 345                 350
    Asp Glu Ala Phe Gln Arg Tyr His Gly Ala Ala Arg Glu Ser Lys Leu
                355                 360                 365

<210> SEQ ID NO 19
<211> LENGTH: 368
<212> TYPE: PRT
<213> ORGANISM: Artificial Sequence
<220> FEATURE:
<223> OTHER INFORMATION: mutant DAAO

<400> SEQUENCE: 19

Met Gly Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
            35                  40                  45

Pro Trp Ala Gly Ala Val Trp Thr Pro Gln Met Thr Leu Thr Asp Gly
        50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
            100                 105                 110
Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
                180                 185                 190

Ala Cys Glu Pro Ile Arg Gly Gln Thr Val Leu Val Lys Ser Pro Cys
                195                 200                 205

Lys Arg Cys Thr Ser Asp Ser Ser Asp Pro Ala Ser Arg Ala Tyr Ile
                210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Cys Ile Ser Ser Asp Gly Thr Ile
                260                 265                 270

Glu Gly Ile Glu Val Leu Arg His Asn Val Gly Leu Arg Pro Ala Arg
                275                 280                 285

Arg Gly Gly Pro Arg Val Glu Ala Glu Arg Ile Ser Leu Pro Leu Asp
290                 295                 300

Arg Thr Lys Ser Pro Leu Ser Leu Gly Arg Gly Ser Tyr Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
                340                 345                 350

Asp Glu Ala Phe Gln Arg Tyr His Gly Ala Ala Arg Glu Ser Lys Leu
                355                 360                 365

<210> SEQ ID NO 20
<211> LENGTH: 368
<212> TYPE: PRT
<213> ORGANISM: Artificial Sequence
<220> FEATURE:
<223> OTHER INFORMATION: mutant DAAO

<400> SEQUENCE: 20

Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
            35                  40                  45

Pro Trp Ala Gly Ala Val Trp Thr Pro Gln Met Thr Leu Thr Asp Gly
        50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
                    100                 105                 110
Pro Asn Tyr Arg Pro Leu Pro Ser Ser Glu Cys Pro Pro Gly Ala Ile
            115                 120                 125

Gly Val Thr Tyr Asp Thr Leu Ser Val His Ala Pro Lys Tyr Cys Gln
            130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Cys Glu Pro Ile Arg Gly Gln Thr Val Leu Val Lys Ser Pro Cys
            195                 200                 205

Lys Arg Cys Thr Ser Asp Ser Ser Asp Pro Ala Ser Pro Ala Tyr Ile
            210                 215                 220

Ile Pro Arg Pro Gly Gly Glu Val Ile Cys Gly Gly Ala Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Cys Ile Ser Ser Asp Gly Thr Ile
            260                 265                 270

Glu Gly Ile Glu Val Leu Arg His Asn Val Gly Leu Arg Pro Ala Arg
            275                 280                 285

Arg Gly Gly Pro Arg Val Glu Ala Glu Arg Ile Ser Leu Pro Leu Asp
290                 295                 300

Arg Thr Lys Ser Pro Leu Ser Leu Gly Arg Gly Ser Tyr Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
            355                 360                 365

<210> SEQ ID NO 21
<211> LENGTH: 368
<212> TYPE: PRT
<213> ORGANISM: Artificial Sequence
<220> FEATURE:
<223> OTHER INFORMATION: mutant DAAO

<400> SEQUENCE: 21

Met Gly Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
            35                  40                  45

Pro Trp Ala Gly Ala Val Trp Thr Pro Gln Met Thr Leu Thr Asp Gly
        50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
            100                 105                 110
Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
                180                 185                 190

Ala Cys Glu Pro Ile Arg Gly Gln Thr Val Leu Val Lys Ser Pro Cys
                195                 200                 205

Lys Arg Cys Thr Ser Asp Ser Ser Asp Pro Ala Ser Pro Ala Tyr Ile
                210                 215                 220

Ile Pro Arg Pro Gly Gly Glu Val Ile Cys Gly Gly Val Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Cys Ile Ser Ser Asp Gly Thr Ile
                260                 265                 270

Glu Gly Ile Glu Val Leu Arg His Asn Val Gly Leu Arg Pro Ala Arg
                275                 280                 285

Arg Gly Gly Pro Arg Val Glu Ala Glu Arg Ile Ser Leu Pro Leu Asp
290                 295                 300

Arg Thr Lys Ser Pro Leu Ser Leu Gly Arg Gly Ser Tyr Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
                340                 345                 350

Asp Glu Ala Phe Gln Arg Tyr His Gly Ala Ala Arg Glu Ser Lys Leu
                355                 360                 365

<210> SEQ ID NO 22
<211> LENGTH: 368
<212> TYPE: PRT
<213> ORGANISM: Artificial Sequence
<220> FEATURE:
<223> OTHER INFORMATION: mutant DAAO

<400> SEQUENCE: 22

Met Gly Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
            35                  40                  45

Pro Trp Ala Gly Ala Val Trp Asn Pro Gln Met Thr Leu Thr Asp Gly
        50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
                 100              105             110
Pro Asn Tyr Arg Pro Leu Pro Ser Ser Glu Cys Pro Pro Gly Ala Ile
            115             120              125

Gly Val Thr Tyr Asp Thr Leu Ser Val His Ala Pro Lys Tyr Cys Gln
130              135              140

Tyr Leu Ala Arg Glu Leu Gln Lys Leu Gly Ala Thr Phe Glu Arg Arg
145              150              155              160

Thr Val Thr Ser Leu Glu Gln Ala Phe Asp Gly Ala Asp Leu Val Val
                165              170              175

Asn Ala Thr Gly Leu Gly Ala Lys Ser Ile Ala Gly Ile Asp Asp Gln
            180              185              190

Ala Cys Glu Pro Ile Arg Gly Gln Thr Val Leu Val Lys Ser Pro Cys
            195              200              205

Lys Arg Cys Thr Ser Asp Ser Ser Asp Pro Ala Ser Pro Ala Tyr Ile
    210              215              220

Ile Pro Arg Pro Gly Gly Glu Val Ile Cys Gly Gly Thr Tyr Gly Val
225              230              235              240

Gly Asp Trp Asp Leu Ser Val Asn Pro Glu Thr Val Gln Arg Ile Leu
                245              250              255

Lys His Cys Leu Arg Leu Asp Pro Cys Ile Ser Ser Asp Gly Thr Ile
            260              265              270

Glu Gly Ile Glu Val Leu Arg His Asn Val Gly Leu Arg Pro Ala Arg
    275              280              285

Arg Gly Gly Pro Arg Val Glu Ala Glu Arg Ile Ser Leu Pro Leu Asp
290              295              300

Arg Thr Lys Ser Pro Leu Ser Leu Gly Arg Gly Ser Tyr Arg Ala Ala
305              310              315              320

Lys Glu Lys Glu Val Thr Leu Val His Ala Tyr Gly Phe Ser Ser Ala
                325              330              335

Gly Tyr Gln Gln Ser Trp Gly Ala Ala Glu Asp Val Ala Gln Leu Val
            340              345              350

Asp Glu Ala Phe Gln Arg Tyr His Gly Ala Ala Arg Glu Ser Lys Leu
            355              360              365

<210> SEQ ID NO 23
<211> LENGTH: 368
<212> TYPE: PRT
<213> ORGANISM: Artificial Sequence
<220> FEATURE:
<223> OTHER INFORMATION: mutant DAAO

<400> SEQUENCE: 23

Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Thr Trp Asn Pro Gln Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
            100                 105                 110
Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
        130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Cys Glu Pro Ile Arg Gly Gln Thr Val Leu Val Lys Ser Pro Cys
        195                 200                 205

Lys Arg Cys Thr Ser Asp Ser Ser Asp Pro Ala Ser Pro Ala Tyr Ile
    210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Cys Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Ser Leu Pro Leu Asp
    290                 295                 300

Arg Thr Lys Ser Pro Leu Ser Leu Gly Arg Gly Ser Tyr Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365

<210> SEQ ID NO 24
<211> LENGTH: 368
<212> TYPE: PRT
<213> ORGANISM: Artificial Sequence
<220> FEATURE:
<223> OTHER INFORMATION: mutant DAAO

<400> SEQUENCE: 24

Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Ile Trp Asn Pro Gln Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
            100                 105                 110
Pro Asn Tyr Arg Pro Leu Pro Ser Ser Glu Cys Pro Gly Ala Ile
        115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Cys Glu Pro Ile Arg Gly Gln Thr Val Leu Val Lys Ser Pro Cys
        195                 200                 205

Lys Arg Cys Thr Ser Asp Ser Ser Asp Pro Ala Ser Pro Ala Tyr Ile
    210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Cys Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Ser Leu Pro Leu Asp
    290                 295                 300

Arg Thr Lys Ser Pro Leu Ser Leu Gly Arg Gly Ser Tyr Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365

<210> SEQ ID NO 25
<211> LENGTH: 368
<212> TYPE: PRT
<213> ORGANISM: Artificial Sequence
<220> FEATURE:
<223> OTHER INFORMATION: mutant DAAO

<400> SEQUENCE: 25

Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Val Trp Asn Pro His Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
                100               105                110
Pro Asn Tyr Arg Pro Leu Pro Ser Ser Glu Cys Pro Pro Gly Ala Ile
            115                 120                 125

Gly Val Thr Tyr Asp Thr Leu Ser Val His Ala Pro Lys Tyr Cys Gln
            130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
            165                 170                 175

Asn Ala Thr Gly Leu Gly Ala Lys Ser Ile Ala Gly Ile Asp Asp Gln
            180                 185                 190

Ala Cys Glu Pro Ile Arg Gly Gln Thr Val Leu Val Lys Ser Pro Cys
            195                 200                 205

Lys Arg Cys Thr Ser Asp Ser Ser Asp Pro Ala Ser Pro Ala Tyr Ile
            210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
            245                 250                 255

Lys His Cys Leu Arg Leu Asp Pro Cys Ile Ser Ser Asp Gly Thr Ile
            260                 265                 270

Glu Gly Ile Glu Val Leu Arg His Asn Val Gly Leu Arg Pro Ala Arg
            275                 280                 285

Arg Gly Gly Pro Arg Val Glu Ala Glu Arg Ile Ser Leu Pro Leu Asp
            290                 295                 300

Arg Thr Lys Ser Pro Leu Ser Leu Gly Arg Gly Ser Tyr Arg Ala Ala
305                 310                 315                 320

Lys Glu Lys Glu Val Thr Leu Val His Ala Tyr Gly Phe Ser Ser Ala
            325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
            355                 360                 365

<210> SEQ ID NO 26
<211> LENGTH: 368
<212> TYPE: PRT
<213> ORGANISM: Artificial Sequence
<220> FEATURE:
<223> OTHER INFORMATION: mutant DAAO

<400> SEQUENCE: 26

Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
            35                  40                  45

Pro Trp Ala Gly Ala Leu Trp Asn Pro Gln Met Thr Leu Thr Asp Gly
50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
            85                  90                  95

Ala Gln Asn Glu Asp Gly Leu Leu Gly His Trp Tyr Lys Asp Ile Thr
```

```
                    100                 105                 110
Pro Asn Tyr Arg Pro Leu Pro Ser Ser Glu Cys Pro Pro Gly Ala Ile
            115                 120                 125

Gly Val Thr Tyr Asp Thr Leu Ser Val His Ala Pro Lys Tyr Cys Gln
            130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Cys Glu Pro Ile Arg Gly Gln Thr Val Leu Val Lys Ser Pro Cys
            195                 200                 205

Lys Arg Cys Thr Ser Asp Ser Ser Asp Pro Ala Ser Pro Ala Tyr Ile
            210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Cys Ile Ser Ser Asp Gly Thr Ile
            260                 265                 270

Glu Gly Ile Glu Val Leu Arg His Asn Val Gly Leu Arg Pro Ala Arg
            275                 280                 285

Arg Gly Gly Pro Arg Val Glu Ala Glu Arg Ile Ser Leu Pro Leu Asp
            290                 295                 300

Arg Thr Lys Ser Pro Leu Ser Leu Gly Arg Gly Ser Tyr Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
            355                 360                 365

<210> SEQ ID NO 27
<211> LENGTH: 368
<212> TYPE: PRT
<213> ORGANISM: Artificial Sequence
<220> FEATURE:
<223> OTHER INFORMATION: mutant DAAO

<400> SEQUENCE: 27

Met Gly Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
            35                  40                  45

Pro Trp Ala Gly Ala Ile Trp Asn Pro His Met Thr Leu Thr Asp Gly
            50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
                100             105             110
Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
        130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
                180                 185                 190

Ala Cys Glu Pro Ile Arg Gly Gln Thr Val Leu Val Lys Ser Pro Cys
            195                 200                 205

Lys Arg Cys Thr Ser Asp Ser Ser Asp Pro Ala Ser Pro Ala Tyr Ile
        210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Cys Ile Ser Ser Asp Gly Thr Ile
                260                 265                 270

Glu Gly Ile Glu Val Leu Arg His Asn Val Gly Leu Arg Pro Ala Arg
            275                 280                 285

Arg Gly Gly Pro Arg Val Glu Ala Glu Arg Ile Ser Leu Pro Leu Asp
        290                 295                 300

Arg Thr Lys Ser Pro Leu Ser Leu Gly Arg Gly Ser Tyr Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
                340                 345                 350

Asp Glu Ala Phe Gln Arg Tyr His Gly Ala Ala Arg Glu Ser Lys Leu
            355                 360                 365

<210> SEQ ID NO 28
<211> LENGTH: 368
<212> TYPE: PRT
<213> ORGANISM: Artificial Sequence
<220> FEATURE:
<223> OTHER INFORMATION: mutant DAAO

<400> SEQUENCE: 28

Met Gly Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
            35                  40                  45

Pro Trp Ala Gly Ala Val Trp Asn Pro His Met Thr Leu Thr Asp Gly
        50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
            100                 105                 110
Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
        130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Cys Glu Pro Ile Arg Gly Gln Thr Val Leu Val Lys Ser Pro Cys
        195                 200                 205

Lys Arg Cys Thr Ser Asp Ser Ser Asp Pro Ala Ser Pro Ala Tyr Ile
        210                 215                 220

Ile Pro Arg Pro Gly Gly Glu Val Ile Cys Gly Gly Val Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Cys Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Ser Leu Pro Leu Asp
        290                 295                 300

Arg Thr Lys Ser Pro Leu Ser Leu Gly Arg Gly Ser Tyr Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365

<210> SEQ ID NO 29
<211> LENGTH: 368
<212> TYPE: PRT
<213> ORGANISM: Artificial Sequence
<220> FEATURE:
<223> OTHER INFORMATION: mutant DAAO

<400> SEQUENCE: 29

Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Val Trp Asn Pro His Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
              100                 105                 110
Pro Asn Tyr Arg Pro Leu Pro Ser Ser Glu Cys Pro Pro Gly Ala Ile
            115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Cys Glu Pro Ile Arg Gly Gln Thr Val Leu Val Lys Ser Pro Cys
        195                 200                 205

Lys Ala Cys Thr Ser Asp Ser Ser Asp Pro Ala Ser Pro Ala Tyr Ile
    210                 215                 220

Ile Pro Arg Pro Gly Gly Glu Val Ile Cys Gly Gly Val Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Cys Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Ser Leu Pro Leu Asp
    290                 295                 300

Arg Thr Lys Ser Pro Leu Ser Leu Gly Arg Gly Ser Tyr Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365

<210> SEQ ID NO 30
<211> LENGTH: 368
<212> TYPE: PRT
<213> ORGANISM: Artificial Sequence
<220> FEATURE:
<223> OTHER INFORMATION: mutant DAAO

<400> SEQUENCE: 30

Met Gly Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Val Trp Asn Pro His Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
```

```
            100                 105                 110
Pro Asn Tyr Arg Pro Leu Pro Ser Ser Glu Cys Pro Pro Gly Ala Ile
            115                 120                 125

Gly Val Thr Tyr Asp Thr Leu Ser Val His Ala Pro Lys Tyr Cys Gln
            130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Cys Glu Pro Ile Arg Gly Gln Thr Val Leu Val Lys Ser Pro Cys
            195                 200                 205

Lys Ala Cys Thr Ser Asp Ser Ser Asp Pro Ala Ser Arg Ala Tyr Ile
            210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Cys Ile Ser Ser Asp Gly Thr Ile
            260                 265                 270

Glu Gly Ile Glu Val Leu Arg His Asn Val Gly Leu Arg Pro Ala Arg
            275                 280                 285

Arg Gly Gly Pro Arg Val Glu Ala Glu Arg Ile Ser Leu Pro Leu Asp
            290                 295                 300

Arg Thr Lys Ser Pro Leu Ser Leu Gly Arg Gly Ser Tyr Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
            355                 360                 365

<210> SEQ ID NO 31
<211> LENGTH: 372
<212> TYPE: PRT
<213> ORGANISM: Artificial Sequence
<220> FEATURE:
<223> OTHER INFORMATION: mutant DAAO

<400> SEQUENCE: 31

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
            35                  40                  45

Pro Trp Ala Gly Ala Leu Trp Asn Pro Gln Met Ser Lys Glu Ala Gly
            50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
```

```
                   100                 105                 110
Pro Asn Tyr Arg His Leu Asn Pro Ser Asp Cys Pro Pro Gly Ala Ile
               115                 120                 125

Gly Val Thr Tyr Asp Thr Leu Ser Val Asn Ala Pro Lys Phe Cys Gln
130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
                180                 185                 190

Glu Val Glu Pro Ile Arg Gly Gln Thr Val Leu Ile Lys Ser Asn Cys
                195                 200                 205

Lys Arg Cys Thr Met Asp Ser Ser Asp Pro Lys Ser Pro Ala Tyr Ile
                210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
                260                 265                 270

Glu Gly Ile Glu Ile Leu Arg His Asn Val Gly Leu Arg Pro Ala Arg
                275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
                340                 345                 350

Val Asp Gln Ala Ile Gly Ser Ser Ser Ser Ala Ser Ser Gly Arg Tyr
                355                 360                 365

Leu Ala Lys Leu
    370

<210> SEQ ID NO 32
<211> LENGTH: 372
<212> TYPE: PRT
<213> ORGANISM: Artificial Sequence
<220> FEATURE:
<223> OTHER INFORMATION: mutant DAAO

<400> SEQUENCE: 32

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
                35                  40                  45

Pro Trp Ala Gly Ala Thr Trp Asn Pro Gln Met Ser Lys Glu Ala Gly
                50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
```

```
            85                  90                  95
Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Cys Thr Met Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 33
<211> LENGTH: 372
<212> TYPE: PRT
<213> ORGANISM: Artificial Sequence
<220> FEATURE:
<223> OTHER INFORMATION: mutant DAAO

<400> SEQUENCE: 33

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Ile Trp Asn Pro His Met Ser Lys Glu Ala Gly
    50                  55                  60

Pro Arg Gln Ala Lys Trp Glu Glu Ala Thr Phe Lys Gln Trp Val Asp
```

```
            65                  70                  75                  80
        Phe Val Pro Gln Gly Leu Ala Met Trp Leu Lys Gly Thr Arg Arg Phe
                            85                  90                  95

Ala Glu Thr Glu Ala Asp Leu Leu Gly His Trp Tyr Lys Asp Ile Val
                        100                 105                 110

Pro Asn Tyr Arg His Leu Asn Pro Ser Asp Cys Pro Gly Ala Ile
                    115                 120                 125

Gly Val Thr Tyr Asp Thr Leu Ser Val Asn Ala Pro Lys Phe Cys Gln
                130                 135                 140

Tyr Leu Gln Arg Glu Ala Gln Lys Leu Gly Val Thr Phe Glu Arg Arg
        145                 150                 155                 160

Leu Val Thr Ser Leu Glu Gln Ile Ala Asp Gly Ala Asp Leu Ile Val
                        165                 170                 175

Asn Ala Thr Gly Leu Gly Ala Lys Ser Ile Ala Gly Val Glu Asp Gln
                    180                 185                 190

Glu Val Glu Pro Ile Arg Gly Gln Thr Val Leu Ile Lys Ser Asn Cys
                195                 200                 205

Lys Arg Cys Thr Met Asp Ser Ser Asp Pro Lys Ser Pro Ala Tyr Ile
        210                 215                 220

Ile Pro Arg Pro Gly Gly Glu Val Ile Cys Gly Gly Thr Tyr Leu Val
        225                 230                 235                 240

Gly Asn Tyr Asp Leu Ser Val Asp Pro Ala Thr Ile Pro Arg Ile Leu
                        245                 250                 255

Lys His Cys Leu Arg Leu Asp Pro Ser Ile Ser Thr Asp Gly Thr Leu
                    260                 265                 270

Glu Gly Ile Glu Ile Leu Arg His Asn Val Gly Leu Arg Pro Ala Arg
                275                 280                 285

Arg Gly Gly Pro Arg Val Glu Leu Glu Arg Val Ser Phe Pro Leu Lys
        290                 295                 300

Arg Gly Gln Ser Leu Leu Ala Leu Gly Thr Ala Lys Ala Ala Glu Gly
        305                 310                 315                 320

Lys Ala Ser Arg Thr Val Pro Val Val His Ala Tyr Gly Phe Ser Ser
                        325                 330                 335

Ala Gly Tyr Gln Gln Gly Trp Gly Ala Ala Leu Glu Val Arg Asp Leu
                    340                 345                 350

Val Asp Gln Ala Ile Gly Ser Ser Ser Ala Ser Ser Gly Arg Tyr
                355                 360                 365

Leu Ala Lys Leu
            370

<210> SEQ ID NO 34
<211> LENGTH: 372
<212> TYPE: PRT
<213> ORGANISM: Artificial Sequence
<220> FEATURE:
<223> OTHER INFORMATION: mutant DAAO

<400> SEQUENCE: 34

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
```

```
                50                  55                  60
Pro Arg Gln Ala Lys Trp Glu Ala Thr Phe Lys Gln Trp Val Asp
 65                  70                  75                  80

Phe Val Pro Gln Gly Leu Ala Met Trp Leu Lys Gly Thr Arg Arg Phe
                 85                  90                  95

Ala Glu Thr Glu Ala Asp Leu Leu Gly His Trp Tyr Lys Asp Ile Val
                100                 105                 110

Pro Asn Tyr Arg His Leu Asn Pro Ser Asp Cys Pro Pro Gly Ala Ile
                115                 120                 125

Gly Val Thr Tyr Asp Thr Leu Ser Val Asn Ala Pro Lys Phe Cys Gln
            130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
            195                 200                 205

Lys Arg Cys Thr Met Asp Ser Ser Asp Pro Lys Ser Pro Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
                260                 265                 270

Glu Gly Ile Glu Ile Leu Arg His Asn Val Gly Leu Arg Pro Ala Arg
            275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
                340                 345                 350

Val Asp Gln Ala Ile Gly Ser Ser Ser Ala Ser Ser Gly Arg Tyr
                355                 360                 365

Leu Ala Lys Leu
        370

<210> SEQ ID NO 35
<211> LENGTH: 372
<212> TYPE: PRT
<213> ORGANISM: Artificial Sequence
<220> FEATURE:
<223> OTHER INFORMATION: mutant DAAO

<400> SEQUENCE: 35

Met Thr Gln Asn Lys Arg Val Val Val Leu Gly Ser Gly Val Ile Gly
 1               5                  10                  15

Leu Ser Cys Ala Leu Ala Leu Gln Lys Gly Tyr Lys Val His Val
                20                  25                  30

Val Ala Arg Asp Leu Pro Glu Asp Thr Val Ala Gln Thr Phe Ala Ser
```

```
                35                  40                  45
Pro Trp Ala Gly Ala Leu Trp Asn Pro Gln Met Ser Lys Glu Ala Gly
 50                  55                  60

Pro Arg Gln Ala Lys Trp Glu Glu Ala Thr Phe Lys Gln Trp Val Asp
 65                  70                  75                  80

Phe Val Pro Gln Gly Leu Ala Met Trp Leu Lys Gly Thr Arg Arg Phe
                 85                  90                  95

Ala Glu Thr Glu Ala Asp Leu Leu Gly His Trp Tyr Lys Asp Ile Val
                100                 105                 110

Pro Asn Tyr Arg His Leu Asn Pro Ser Asp Cys Pro Pro Gly Ala Ile
                115                 120                 125

Gly Val Thr Tyr Asp Thr Leu Ser Val Asn Ala Pro Lys Phe Cys Gln
                130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
                180                 185                 190

Glu Val Glu Pro Ile Arg Gly Gln Thr Val Leu Ile Lys Ser Asn Cys
                195                 200                 205

Lys Arg Cys Thr Ser Asp Ser Ser Asp Pro Lys Ser Pro Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
                260                 265                 270

Glu Gly Ile Glu Ile Leu Arg His Asn Val Gly Leu Arg Pro Ala Arg
                275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val His Ala Tyr Gly Phe Ser Ser
                325                 330                 335

Ala Gly Tyr Gln Gln Gly Trp Gly Ala Ala Leu Glu Val Arg Asp Leu
                340                 345                 350

Val Asp Gln Ala Ile Gly Ser Ser Ser Ala Ser Ser Gly Arg Tyr
                355                 360                 365

Leu Ala Lys Leu
    370

<210> SEQ ID NO 36
<211> LENGTH: 372
<212> TYPE: PRT
<213> ORGANISM: Artificial Sequence
<220> FEATURE:
<223> OTHER INFORMATION: mutant DAAO

<400> SEQUENCE: 36

Met Thr Gln Asn Lys Arg Val Val Val Leu Gly Ser Gly Val Ile Gly
 1               5                  10                  15

Leu Ser Cys Ala Leu Ala Leu Ala Gln Lys Gly Tyr Lys Val His Val
```

20                  25                  30
Val Ala Arg Asp Leu Pro Glu Asp Thr Val Ala Gln Thr Phe Ala Ser
        35                  40                  45

Pro Trp Ala Gly Ala Thr Trp Asn Pro Gln Met Ser Lys Glu Ala Gly
 50                  55                  60

Pro Arg Gln Ala Lys Trp Glu Glu Ala Thr Phe Lys Gln Trp Val Asp
 65                  70                  75                  80

Phe Val Pro Gln Gly Leu Ala Met Trp Leu Lys Gly Thr Arg Arg Phe
                 85                  90                  95

Ala Glu Thr Glu Ala Asp Leu Leu Gly His Trp Tyr Lys Asp Ile Val
                100                 105                 110

Pro Asn Tyr Arg His Leu Asn Pro Ser Asp Cys Pro Pro Gly Ala Ile
            115                 120                 125

Gly Val Thr Tyr Asp Thr Leu Ser Val Asn Ala Pro Lys Phe Cys Gln
        130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Cys Thr Ser Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ser Ala Ser Ser Gly Arg Tyr
        355                 360                 365

Leu Ala Lys Leu
    370

<210> SEQ ID NO 37
<211> LENGTH: 372
<212> TYPE: PRT
<213> ORGANISM: Artificial Sequence
<220> FEATURE:
<223> OTHER INFORMATION: mutant DAAO

<400> SEQUENCE: 37

Met Thr Gln Asn Lys Arg Val Val Val Leu Gly Ser Gly Val Ile Gly

-continued

```
1               5                   10                  15
Leu Ser Cys Ala Leu Ala Leu Ala Gln Lys Gly Tyr Lys Val His Val
                20                  25                  30
Val Ala Arg Asp Leu Pro Glu Asp Thr Val Ala Gln Thr Phe Ala Ser
                35                  40                  45
Pro Trp Ala Gly Ala Ile Trp Asn Pro His Met Ser Lys Glu Ala Gly
                50                  55                  60
Pro Arg Gln Ala Lys Trp Glu Glu Ala Thr Phe Lys Gln Trp Val Asp
65              70                  75                  80
Phe Val Pro Gln Gly Leu Ala Met Trp Leu Lys Gly Thr Arg Arg Phe
                85                  90                  95
Ala Glu Thr Glu Ala Asp Leu Leu Gly His Trp Tyr Lys Asp Ile Val
                100                 105                 110
Pro Asn Tyr Arg His Leu Asn Pro Ser Asp Cys Pro Pro Gly Ala Ile
                115                 120                 125
Gly Val Thr Tyr Asp Thr Leu Ser Val Asn Ala Pro Lys Phe Cys Gln
                130                 135                 140
Tyr Leu Gln Arg Glu Ala Gln Lys Leu Gly Val Thr Phe Glu Arg Arg
145             150                 155                 160
Leu Val Thr Ser Leu Glu Gln Ile Ala Asp Gly Ala Asp Leu Ile Val
                165                 170                 175
Asn Ala Thr Gly Leu Gly Ala Lys Ser Ile Ala Gly Val Glu Asp Gln
                180                 185                 190
Glu Val Glu Pro Ile Arg Gly Gln Thr Val Leu Ile Lys Ser Asn Cys
                195                 200                 205
Lys Arg Cys Thr Ser Asp Ser Ser Asp Pro Lys Ser Pro Ala Tyr Ile
                210                 215                 220
Ile Pro Arg Pro Gly Gly Glu Val Ile Cys Gly Gly Thr Tyr Leu Val
225             230                 235                 240
Gly Asn Tyr Asp Leu Ser Val Asp Pro Ala Thr Ile Pro Arg Ile Leu
                245                 250                 255
Lys His Cys Leu Arg Leu Asp Pro Ser Ile Ser Thr Asp Gly Thr Leu
                260                 265                 270
Glu Gly Ile Glu Ile Leu Arg His Asn Val Gly Leu Arg Pro Ala Arg
                275                 280                 285
Arg Gly Gly Pro Arg Val Glu Leu Glu Arg Val Ser Phe Pro Leu Lys
                290                 295                 300
Arg Gly Gln Ser Leu Leu Ala Leu Gly Thr Ala Lys Ala Ala Glu Gly
305             310                 315                 320
Lys Ala Ser Arg Thr Val Pro Val Val His Ala Tyr Gly Phe Ser Ser
                325                 330                 335
Ala Gly Tyr Gln Gln Gly Trp Gly Ala Ala Leu Glu Val Arg Asp Leu
                340                 345                 350
Val Asp Gln Ala Ile Gly Ser Ser Ser Ala Ser Ser Gly Arg Tyr
                355                 360                 365
Leu Ala Lys Leu
    370
```

<210> SEQ ID NO 38
<211> LENGTH: 372
<212> TYPE: PRT
<213> ORGANISM: Artificial Sequence
<220> FEATURE:
<223> OTHER INFORMATION: mutant DAAO

```
<400> SEQUENCE: 38

Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
    50                  55                  60

Pro Arg Gln Ala Lys Trp Glu Ala Thr Phe Lys Gln Trp Val Asp
65              70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Cys Thr Ser Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 39
<211> LENGTH: 372
<212> TYPE: PRT
<213> ORGANISM: Artificial Sequence
```

```
<220> FEATURE:
<223> OTHER INFORMATION: mutant DAAO

<400> SEQUENCE: 39

Met Cys Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
        50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Cys Thr Ser Asp Ser Ser Asp Pro Lys Ser Pro Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 40
```

```
<211> LENGTH: 372
<212> TYPE: PRT
<213> ORGANISM: Artificial Sequence
<220> FEATURE:
<223> OTHER INFORMATION: mutant DAAO

<400> SEQUENCE: 40

Met Ser Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
                100                 105                 110

Pro Asn Tyr Arg His Leu Asn Pro Ser Asp Cys Pro Pro Gly Ala Ile
            115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
                180                 185                 190

Glu Val Glu Pro Ile Arg Gly Gln Thr Val Leu Ile Lys Ser Asn Cys
            195                 200                 205

Lys Arg Cys Thr Ser Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
                260                 265                 270

Glu Gly Ile Glu Ile Leu Arg His Asn Val Gly Leu Arg Pro Ala Arg
            275                 280                 285

Arg Gly Gly Pro Arg Val Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
                340                 345                 350

Val Asp Gln Ala Ile Gly Ser Ser Ser Ala Ser Ser Gly Arg Tyr
            355                 360                 365

Leu Ala Lys Leu
    370
```

<210> SEQ ID NO 41
<211> LENGTH: 372
<212> TYPE: PRT
<213> ORGANISM: Artificial Sequence
<220> FEATURE:
<223> OTHER INFORMATION: mutant DAAO

<400> SEQUENCE: 41

```
Met Thr Gln Asn Lys Arg Val Val Leu Gly Ser Gly Val Ile Gly
1               5                  10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Tyr Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Cys Thr Ser Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365
```

Leu Ala Lys Leu
    370

<210> SEQ ID NO 42
<211> LENGTH: 372
<212> TYPE: PRT
<213> ORGANISM: Artificial Sequence
<220> FEATURE:
<223> OTHER INFORMATION: mutant DAAO

<400> SEQUENCE: 42

Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Val Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Cys Thr Ser Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 43
<211> LENGTH: 372
<212> TYPE: PRT
<213> ORGANISM: Artificial Sequence
<220> FEATURE:
<223> OTHER INFORMATION: mutant DAAO

<400> SEQUENCE: 43

Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Thr Val Glu Pro Ile Arg Gly Gln Thr Val Leu Ile Lys Ser Asn Cys
        195                 200                 205

Lys Arg Cys Thr Ser Asp Ser Ser Asp Pro Lys Ser Pro Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

```
Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 44
<211> LENGTH: 372
<212> TYPE: PRT
<213> ORGANISM: Artificial Sequence
<220> FEATURE:
<223> OTHER INFORMATION: mutant DAAO

<400> SEQUENCE: 44

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Cys Thr Ser Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Thr Phe Pro Leu Lys
    290                 295                 300

Arg Gly Gln Ser Leu Leu Ala Leu Gly Thr Ala Lys Ala Ala Glu Gly
305                 310                 315                 320
```

```
Lys Ala Ser Arg Thr Val Pro Val His Ala Tyr Gly Phe Ser Ser
            325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
            355                 360                 365

Leu Ala Lys Leu
    370

<210> SEQ ID NO 45
<211> LENGTH: 372
<212> TYPE: PRT
<213> ORGANISM: Artificial Sequence
<220> FEATURE:
<223> OTHER INFORMATION: mutant DAAO

<400> SEQUENCE: 45

Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
            115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
            195                 200                 205

Lys Arg Cys Thr Ser Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
            275                 280                 285

Arg Gly Gly Pro Arg Val Glu Leu Glu Arg Val Ser Phe Pro Leu Lys
    290                 295                 300
```

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
            325                 330                 335

Ser Gly Tyr Gln Gln Gly Trp Gly Ala Ala Leu Glu Val Arg Asp Leu
        340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 46
<211> LENGTH: 372
<212> TYPE: PRT
<213> ORGANISM: Artificial Sequence
<220> FEATURE:
<223> OTHER INFORMATION: mutant DAAO

<400> SEQUENCE: 46

Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
    50                  55                  60

Pro Arg Gln Ala Lys Trp Glu Glu Ala Thr Phe Lys Gln Trp Val Asp
65              70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
            165                 170                 175

Asn Ala Thr Gly Leu Gly Ala Lys Ser Ile Ala Gly Val Glu Asp Gln
        180                 185                 190

Glu Val Glu Pro Ile Arg Gly Gln Thr Val Leu Ile Lys Ser Asn Cys
    195                 200                 205

Lys Arg Cys Thr Ser Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

```
Arg Gly Gly Pro Arg Val Glu Leu Glu Arg Val Ser Phe Pro Leu Lys
            290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Ser Trp Gly Ala Ala Leu Glu Val Arg Asp Leu
            340                 345                 350

Val Asp Gln Ala Ile Gly Ser Ser Ser Ala Ser Ser Gly Arg Tyr
            355                 360                 365

Leu Ala Lys Leu
    370

<210> SEQ ID NO 47
<211> LENGTH: 372
<212> TYPE: PRT
<213> ORGANISM: Artificial Sequence
<220> FEATURE:
<223> OTHER INFORMATION: mutant DAAO

<400> SEQUENCE: 47

Met Ser Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
50                  55                  60

Pro Arg Gln Ala Lys Trp Glu Glu Ala Thr Phe Lys Gln Trp Val Asp
65                  70                  75                  80

Tyr Val Pro Gln Gly Leu Ala Met Trp Leu Lys Gly Thr Arg Arg Phe
                85                  90                  95

Val Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
            115                 120                 125

Gly Val Thr Tyr Asp Thr Leu Ser Val Asn Ala Pro Lys Phe Cys Gln
            130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Thr Val Glu Pro Ile Arg Gly Gln Thr Val Leu Ile Lys Ser Asn Cys
            195                 200                 205

Lys Arg Cys Thr Ser Asp Ser Ser Asp Pro Lys Ser Pro Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270
```

```
Glu Gly Ile Glu Ile Leu Arg His Asn Val Gly Leu Arg Pro Ala Arg
            275                 280                 285

Arg Gly Gly Pro Arg Val Glu Leu Glu Arg Val Ser Phe Pro Leu Lys
        290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val His Ala Tyr Gly Phe Ser Ser
                325                 330                 335

Ser Gly Tyr Gln Gln Gly Trp Gly Ala Ala Leu Glu Val Arg Asp Leu
                340                 345                 350

Val Asp Gln Ala Ile Gly Ser Ser Ser Ala Ser Ser Gly Arg Tyr
                355                 360                 365

Leu Ala Lys Leu
    370
```

<210> SEQ ID NO 48
<211> LENGTH: 372
<212> TYPE: PRT
<213> ORGANISM: Artificial Sequence
<220> FEATURE:
<223> OTHER INFORMATION: mutant DAAO

<400> SEQUENCE: 48

```
Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Val Glu Thr Glu Ala Asp Leu Leu Gly His Trp Tyr Lys Asp Ile Val
                100                 105                 110

Pro Asn Tyr Arg His Leu Asn Pro Ser Asp Cys Pro Pro Gly Ala Ile
            115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
                180                 185                 190

Ala Val Glu Pro Ile Arg Gly Gln Thr Val Leu Ile Lys Ser Asn Cys
            195                 200                 205

Lys Arg Cys Thr Ser Asp Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255
```

```
Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
            275                 280                 285

Arg Gly Gly Pro Arg Val Glu Leu Glu Arg Val Ser Phe Pro Leu Lys
            290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
            325                 330                 335

Ser Gly Tyr Gln Gln His Trp Gly Ala Ala Leu Glu Val Arg Asp Leu
            340                 345                 350

Val Asp Gln Ala Ile Gly Ser Ser Ser Ala Ser Ser Gly Arg Tyr
            355                 360                 365

Leu Ala Lys Leu
            370

<210> SEQ ID NO 49
<211> LENGTH: 372
<212> TYPE: PRT
<213> ORGANISM: Artificial Sequence
<220> FEATURE:
<223> OTHER INFORMATION: mutant DAAO

<400> SEQUENCE: 49

Met Cys Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
            50                  55                  60

Pro Arg Gln Ala Lys Trp Glu Glu Ala Thr Phe Lys Gln Trp Val Asp
65                  70                  75                  80

Tyr Val Pro Gln Gly Leu Ala Met Trp Leu Lys Gly Thr Arg Arg Phe
            85                  90                  95

Val Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
            115                 120                 125

Gly Val Thr Tyr Asp Thr Leu Ser Val Asn Ala Pro Lys Phe Cys Gln
            130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
            165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
            195                 200                 205

Lys Arg Cys Thr Ser Asp Ser Ser Asp Pro Ser Pro Ala Tyr Ile
            210                 215                 220

Ile Pro Arg Pro Gly Gly Glu Val Ile Cys Gly Gly Thr Tyr Leu Val
225                 230                 235                 240
```

Gly Asn Tyr Asp Leu Ser Val Asp Pro Ala Thr Ile Pro Arg Ile Leu
            245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
            275                 280                 285

Arg Gly Gly Pro Arg Val Glu Leu Glu Arg Val Ser Phe Pro Leu Lys
            290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
            325                 330                 335

Ser Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
            355                 360                 365

Leu Ala Lys Leu
    370

<210> SEQ ID NO 50
<211> LENGTH: 372
<212> TYPE: PRT
<213> ORGANISM: Artificial Sequence
<220> FEATURE:
<223> OTHER INFORMATION: mutant DAAO

<400> SEQUENCE: 50

Met Cys Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Tyr Val Pro Gln Gly Leu Ala Met Trp Leu Lys Gly Thr Arg Arg Phe
            85                  90                  95

Val Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
            115                 120                 125

Gly Val Thr Tyr Asp Thr Leu Ser Val Asn Ala Pro Lys Phe Cys Gln
            130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
            165                 170                 175

Asn Ala Thr Gly Leu Gly Ala Lys Ser Ile Ala Gly Val Glu Asp Gln
            180                 185                 190

Ala Val Glu Pro Ile Arg Gly Gln Thr Val Leu Ile Lys Ser Asn Cys
            195                 200                 205

Lys Arg Cys Thr Ser Asp Ser Ser Asp Pro Lys Ser Pro Ala Tyr Ile
            210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
            245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
            275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ser Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
            355                 360                 365

Leu Ala Lys Leu
    370

<210> SEQ ID NO 51
<211> LENGTH: 372
<212> TYPE: PRT
<213> ORGANISM: Artificial Sequence
<220> FEATURE:
<223> OTHER INFORMATION: mutant DAAO

<400> SEQUENCE: 51

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Val Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Thr Val Glu Pro Ile Arg Gly Gln Thr Val Leu Ile Lys Ser Asn Cys
        195                 200                 205

Lys Arg Cys Thr Ser Asp Ser Asp Pro Lys Ser Pro Ala Tyr Ile
            210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
            245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
            275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
            325                 330                 335

Ser Gly Tyr Gln Gln His Trp Gly Ala Ala Leu Glu Val Arg Asp Leu
            340                 345                 350

Val Asp Gln Ala Ile Gly Ser Ser Ser Ala Ser Ser Gly Arg Tyr
            355                 360                 365

Leu Ala Lys Leu
    370

<210> SEQ ID NO 52
<211> LENGTH: 372
<212> TYPE: PRT
<213> ORGANISM: Artificial Sequence
<220> FEATURE:
<223> OTHER INFORMATION: mutant DAAO

<400> SEQUENCE: 52

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Tyr Val Pro Gln Gly Leu Ala Met Trp Leu Lys Gly Thr Arg Arg Phe
                85                  90                  95

Val Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

```
Thr Val Glu Pro Ile Arg Gly Gln Thr Val Leu Ile Lys Ser Asn Cys
            195                 200                 205

Lys Arg Cys Thr Ser Asp Ser Ser Asp Pro Lys Ser Pro Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
            275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ser Gly Tyr Gln Gln His Trp Gly Ala Ala Leu Glu Val Arg Asp Leu
            340                 345                 350

Val Asp Gln Ala Ile Gly Ser Ser Ser Ala Ser Ser Gly Arg Tyr
            355                 360                 365

Leu Ala Lys Leu
        370

<210> SEQ ID NO 53
<211> LENGTH: 372
<212> TYPE: PRT
<213> ORGANISM: Artificial Sequence
<220> FEATURE:
<223> OTHER INFORMATION: mutant DAAO

<400> SEQUENCE: 53

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Val Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
            115                 120                 125

Gly Val Thr Tyr Asp Thr Leu Ser Val Asn Ala Pro Lys Phe Cys Gln
        130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175
```

Asn Ala Thr Gly Leu Gly Ala Lys Ser Ile Ala Gly Val Glu Asp Gln
            180                 185                 190

Thr Val Glu Pro Ile Arg Gly Gln Thr Val Leu Ile Lys Ser Asn Cys
            195                 200                 205

Lys Arg Cys Thr Ser Asp Ser Asp Pro Lys Ser Pro Ala Tyr Ile
            210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
            275                 280                 285

Arg Gly Gly Pro Arg Val Glu Leu Glu Arg Val Thr Phe Pro Leu Lys
            290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ser Gly Tyr Gln Gln His Trp Gly Ala Ala Leu Glu Val Arg Asp Leu
            340                 345                 350

Val Asp Gln Ala Ile Gly Ser Ser Ser Ala Ser Ser Gly Arg Tyr
            355                 360                 365

Leu Ala Lys Leu
            370

<210> SEQ ID NO 54
<211> LENGTH: 372
<212> TYPE: PRT
<213> ORGANISM: Artificial Sequence
<220> FEATURE:
<223> OTHER INFORMATION: mutant DAAO

<400> SEQUENCE: 54

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
50                  55                  60

Pro Arg Gln Ala Lys Trp Glu Glu Ala Thr Phe Lys Gln Trp Val Asp
65                  70                  75                  80

Tyr Val Pro Gln Gly Leu Ala Met Trp Leu Lys Gly Thr Arg Arg Phe
                85                  90                  95

Val Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
            115                 120                 125

Gly Val Thr Tyr Asp Thr Leu Ser Val Asn Ala Pro Lys Phe Cys Gln
            130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
            165                 170                 175

Asn Ala Thr Gly Leu Gly Ala Lys Ser Ile Ala Gly Val Glu Asp Gln
            180                 185                 190

Thr Val Glu Pro Ile Arg Gly Gln Thr Val Leu Ile Lys Ser Asn Cys
            195                 200                 205

Lys Arg Cys Thr Ser Asp Ser Ser Asp Pro Lys Ser Pro Ala Tyr Ile
    210                 215                 220

Ile Pro Arg Pro Gly Gly Glu Val Ile Cys Gly Thr Tyr Leu Val
225                 230                 235                 240

Gly Asn Tyr Asp Leu Ser Val Asp Pro Ala Thr Ile Pro Arg Ile Leu
            245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
            275                 280                 285

Arg Gly Gly Pro Arg Val Glu Leu Glu Arg Val Thr Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
            325                 330                 335

Ser Gly Tyr Gln Gln His Trp Gly Ala Ala Leu Glu Val Arg Asp Leu
            340                 345                 350

Val Asp Gln Ala Ile Gly Ser Ser Ser Ala Ser Ser Gly Arg Tyr
            355                 360                 365

Leu Ala Lys Leu
        370

<210> SEQ ID NO 55
<211> LENGTH: 372
<212> TYPE: PRT
<213> ORGANISM: Artificial Sequence
<220> FEATURE:
<223> OTHER INFORMATION: mutant DAAO

<400> SEQUENCE: 55

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
        50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
            85                  90                  95

Val Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
            115                 120                 125

Gly Val Thr Tyr Asp Thr Leu Ser Val Asn Ala Pro Lys Phe Cys Gln
        130                 135                 140

```
Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
            165                 170                 175

Asn Ala Thr Gly Leu Gly Ala Lys Ser Ile Ala Gly Val Glu Asp Gln
        180                 185                 190

Thr Val Glu Pro Ile Arg Gly Gln Thr Val Leu Ile Lys Ser Asn Cys
    195                 200                 205

Lys Ala Cys Thr Ser Asp Ser Ser Asp Pro Lys Ser Pro Ala Tyr Ile
210                 215                 220

Ile Pro Arg Pro Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
            245                 250                 255

Lys His Cys Leu Arg Leu Asp Pro Ser Ile Ser Thr Asp Gly Thr Leu
        260                 265                 270

Glu Gly Ile Glu Ile Leu Arg His Asn Val Gly Leu Arg Pro Ala Arg
    275                 280                 285

Arg Gly Gly Pro Arg Val Glu Leu Glu Arg Val Thr Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
            325                 330                 335

Ser Gly Tyr Gln Gln His Trp Gly Ala Ala Leu Glu Val Arg Asp Leu
        340                 345                 350

Val Asp Gln Ala Ile Gly Ser Ser Ser Ala Ser Ser Gly Arg Tyr
    355                 360                 365

Leu Ala Lys Leu
    370

<210> SEQ ID NO 56
<211> LENGTH: 372
<212> TYPE: PRT
<213> ORGANISM: Artificial Sequence
<220> FEATURE:
<223> OTHER INFORMATION: mutant DAAO

<400> SEQUENCE: 56

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Val Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125
```

```
Gly Val Thr Tyr Asp Thr Leu Ser Val Asn Ala Pro Lys Phe Cys Gln
            130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Thr Val Glu Pro Ile Arg Gly Gln Thr Val Leu Ile Lys Ser Asn Cys
        195                 200                 205

Lys Arg Cys Thr Ser Asp Ser Ser Asp Pro Lys Ser Arg Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Thr Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ser Gly Tyr Gln Gln His Trp Gly Ala Ala Leu Glu Val Arg Asp Leu
            340                 345                 350

Val Asp Gln Ala Ile Gly Ser Ser Ser Ser Ala Ser Ser Gly Arg Tyr
        355                 360                 365

Leu Ala Lys Leu
    370

<210> SEQ ID NO 57
<211> LENGTH: 372
<212> TYPE: PRT
<213> ORGANISM: Artificial Sequence
<220> FEATURE:
<223> OTHER INFORMATION: mutant DAAO

<400> SEQUENCE: 57

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Val Glu Thr Glu Ala Asp Leu Leu Gly His Trp Tyr Lys Asp Ile Val
            100                 105                 110
```

```
Pro Asn Tyr Arg His Leu Asn Pro Ser Asp Cys Pro Pro Gly Ala Ile
            115                 120                 125
Gly Val Thr Tyr Asp Thr Leu Ser Val Asn Ala Pro Lys Phe Cys Gln
        130                 135                 140
Tyr Leu Gln Arg Glu Ala Gln Lys Leu Gly Val Thr Phe Glu Arg Arg
145                 150                 155                 160
Leu Val Thr Ser Leu Glu Gln Ile Ala Asp Gly Ala Asp Leu Ile Val
                165                 170                 175
Asn Ala Thr Gly Leu Gly Ala Lys Ser Ile Ala Gly Val Glu Asp Gln
            180                 185                 190
Thr Val Glu Pro Ile Arg Gly Gln Thr Val Leu Ile Lys Ser Asn Cys
        195                 200                 205
Lys Ala Cys Thr Ser Asp Ser Ser Asp Pro Lys Ser Arg Ala Tyr Ile
    210                 215                 220
Ile Pro Arg Pro Gly Gly Glu Val Ile Cys Gly Gly Thr Tyr Leu Val
225                 230                 235                 240
Gly Asn Tyr Asp Leu Ser Val Asp Pro Ala Thr Ile Pro Arg Ile Leu
                245                 250                 255
Lys His Cys Leu Arg Leu Asp Pro Ser Ile Ser Thr Asp Gly Thr Leu
            260                 265                 270
Glu Gly Ile Glu Ile Leu Arg His Asn Val Gly Leu Arg Pro Ala Arg
        275                 280                 285
Arg Gly Gly Pro Arg Val Glu Leu Glu Arg Val Thr Phe Pro Leu Lys
    290                 295                 300
Arg Gly Gln Ser Leu Leu Ala Leu Gly Thr Ala Lys Ala Ala Glu Gly
305                 310                 315                 320
Lys Ala Ser Arg Thr Val Pro Val Val His Ala Tyr Gly Phe Ser Ser
                325                 330                 335
Ser Gly Tyr Gln Gln His Trp Gly Ala Ala Leu Glu Val Arg Asp Leu
            340                 345                 350
Val Asp Gln Ala Ile Gly Ser Ser Ser Ala Ser Ser Gly Arg Tyr
        355                 360                 365
Leu Ala Lys Leu
    370

<210> SEQ ID NO 58
<211> LENGTH: 372
<212> TYPE: PRT
<213> ORGANISM: Artificial Sequence
<220> FEATURE:
<223> OTHER INFORMATION: mutant DAAO

<400> SEQUENCE: 58

Met Ala Pro Ser Lys Arg Val Val Val Leu Gly Ser Gly Val Val Gly
1               5                   10                  15
Leu Ser Ser Ala Leu Thr Leu Ala Gln Lys Gly Tyr Ser Val His Val
            20                  25                  30
Val Ala Arg Asp Leu Pro Glu Asp Thr Val Ala Gln Thr Phe Ala Ser
        35                  40                  45
Pro Trp Ala Gly Ala Asn Trp Thr Pro Lys Met Ser Lys Glu Asp Gly
    50                  55                  60
Pro Arg Gln Ala Lys Trp Glu Thr Ala Thr Phe Asn Gln Trp Val Asp
65                  70                  75                  80
Leu Val Pro Gln Gly Leu Ala Met Trp Leu Lys Gly Thr Arg Arg Tyr
                85                  90                  95
```

```
Ala Gln Asp Glu Ala Gly Leu Leu Gly His Trp Tyr Gln His Ile Thr
            100                 105                 110

Pro Asn Tyr Arg Lys Leu Glu Ser Glu Cys Pro Pro Gly Ala Ile
        115                 120                 125

Gly Val Thr Tyr Asp Thr Leu Ser Val Asn Ala Pro Lys Phe Cys Gln
130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Glu Gly Phe Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Val Lys Ser Asp Cys
        195                 200                 205

Lys Arg Cys Thr Thr Asp Ser Ser Asp Pro Asn Ser Pro Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Pro Thr Ile Asn Arg Ile Leu
                245                 250                 255

Gln His Cys Leu Arg Leu Asp Pro Ser Ile Ser Thr Asp Gly Thr Leu
            260                 265                 270

Glu Gly Ile Glu Ile Val Arg His Asn Val Gly Leu Arg Pro Ala Arg
        275                 280                 285

Arg Gly Gly Pro Arg Val Glu Val Arg Val Ala Phe Pro Leu Glu
290                 295                 300

Arg Gly Lys Ser Lys Leu Ser Leu Gly Thr Ala Arg Ala Asp Ser Ser
305                 310                 315                 320

Lys Pro Arg Arg Glu Val Pro Val Val His Ala Tyr Gly Phe Ser Ser
                325                 330                 335

Ala Gly Tyr Gln Gln Gly Trp Gly Ala Ala Leu Glu Val Ala Glu Leu
            340                 345                 350

Val Glu Gly Ala Ile Gly Ala Ala Pro Ala Arg Ser Ser His Arg Trp
        355                 360                 365

Leu Ser Lys Leu
    370

<210> SEQ ID NO 59
<211> LENGTH: 372
<212> TYPE: PRT
<213> ORGANISM: Artificial Sequence
<220> FEATURE:
<223> OTHER INFORMATION: mutant DAAO

<400> SEQUENCE: 59

Met Ala Pro Ser Lys Arg Val Val Val Leu Gly Ser Gly Val Val Gly
1               5                   10                  15

Leu Ser Ser Ala Leu Thr Leu Ala Gln Lys Gly Tyr Ser Val His Val
            20                  25                  30

Val Ala Arg Asp Leu Pro Glu Asp Thr Val Ala Gln Thr Phe Ala Ser
        35                  40                  45

Pro Trp Ala Gly Ala Leu Trp Asn Pro Gln Met Ser Lys Glu Asp Gly
    50                  55                  60

Pro Arg Gln Ala Lys Trp Glu Thr Ala Thr Phe Asn Gln Trp Val Asp
65                  70                  75                  80
```

Leu Val Pro Gln Gly Leu Ala Met Trp Leu Lys Gly Thr Arg Arg Tyr
            85                  90                  95

Ala Gln Asp Glu Ala Gly Leu Leu Gly His Trp Tyr Gln His Ile Thr
                100                 105                 110

Pro Asn Tyr Arg Lys Leu Glu Ser Ser Glu Cys Pro Pro Gly Ala Ile
            115                 120                 125

Gly Val Thr Tyr Asp Thr Leu Ser Val Asn Ala Pro Lys Phe Cys Gln
            130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Glu Gly Gly Phe Asp Leu Ile Val
            165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Val Lys Ser Asp Cys
            195                 200                 205

Lys Arg Cys Thr Ser Asp Ser Ser Asp Pro Asn Ser Pro Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Pro Thr Ile Asn Arg Ile Leu
            245                 250                 255

Gln His Cys Leu Arg Leu Asp Pro Ser Ile Ser Thr Asp Gly Thr Leu
            260                 265                 270

Glu Gly Ile Glu Ile Val Arg His Asn Val Gly Leu Arg Pro Ala Arg
            275                 280                 285

Arg Gly Gly Pro Arg Val Glu Val Arg Val Ala Phe Pro Leu Glu
            290                 295                 300

Arg Gly Lys Ser Lys Leu Ser Leu Gly Thr Ala Arg Ala Asp Ser Ser
305                 310                 315                 320

Lys Pro Arg Arg Glu Val Pro Val Val His Ala Tyr Gly Phe Ser Ser
            325                 330                 335

Ala Gly Tyr Gln Gln Gly Trp Gly Ala Ala Leu Glu Val Ala Glu Leu
            340                 345                 350

Val Glu Gly Ala Ile Gly Ala Ala Pro Ala Arg Ser Ser His Arg Trp
            355                 360                 365

Leu Ser Lys Leu
    370

<210> SEQ ID NO 60
<211> LENGTH: 372
<212> TYPE: PRT
<213> ORGANISM: Artificial Sequence
<220> FEATURE:
<223> OTHER INFORMATION: mutant DAAO

<400> SEQUENCE: 60

Met Ala Pro Ser Lys Arg Val Val Val Leu Gly Ser Gly Val Val Gly
1               5                   10                  15

Leu Ser Ser Ala Leu Thr Leu Ala Gln Lys Gly Tyr Ser Val His Val
            20                  25                  30

Val Ala Arg Asp Leu Pro Glu Asp Thr Val Ala Gln Thr Phe Ala Ser
            35                  40                  45

Pro Trp Ala Gly Ala Thr Trp Asn Pro Gln Met Ser Lys Glu Asp Gly
        50                  55                  60

```
Pro Arg Gln Ala Lys Trp Glu Thr Ala Thr Phe Asn Gln Trp Val Asp
 65                  70                  75                  80

Leu Val Pro Gln Gly Leu Ala Met Trp Leu Lys Gly Thr Arg Arg Tyr
                 85                  90                  95

Ala Gln Asp Glu Ala Gly Leu Leu Gly His Trp Tyr Gln His Ile Thr
            100                 105                 110

Pro Asn Tyr Arg Lys Leu Glu Ser Ser Glu Cys Pro Pro Gly Ala Ile
        115                 120                 125

Gly Val Thr Tyr Asp Thr Leu Ser Val Asn Ala Pro Lys Phe Cys Gln
130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Glu Gly Gly Phe Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Val Lys Ser Asp Cys
        195                 200                 205

Lys Arg Cys Thr Ser Asp Ser Ser Asp Pro Asn Ser Pro Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Pro Thr Ile Asn Arg Ile Leu
                245                 250                 255

Gln His Cys Leu Arg Leu Asp Pro Ser Ile Ser Thr Asp Gly Thr Leu
            260                 265                 270

Glu Gly Ile Glu Ile Val Arg His Asn Val Gly Leu Arg Pro Ala Arg
        275                 280                 285

Arg Gly Gly Pro Arg Val Glu Val Glu Arg Val Ala Phe Pro Leu Glu
290                 295                 300

Arg Gly Lys Ser Lys Leu Ser Leu Gly Thr Ala Arg Ala Asp Ser Ser
305                 310                 315                 320

Lys Pro Arg Arg Glu Val Pro Val Val His Ala Tyr Gly Phe Ser Ser
                325                 330                 335

Ala Gly Tyr Gln Gln Gly Trp Gly Ala Ala Leu Glu Val Ala Glu Leu
            340                 345                 350

Val Glu Gly Ala Ile Gly Ala Ala Pro Ala Arg Ser Ser His Arg Trp
        355                 360                 365

Leu Ser Lys Leu
    370

<210> SEQ ID NO 61
<211> LENGTH: 372
<212> TYPE: PRT
<213> ORGANISM: Artificial Sequence
<220> FEATURE:
<223> OTHER INFORMATION: mutant DAAO

<400> SEQUENCE: 61

Met Ala Pro Ser Lys Arg Val Val Val Leu Gly Ser Gly Val Val Gly
  1               5                  10                  15

Leu Ser Ser Ala Leu Thr Leu Ala Gln Lys Gly Tyr Ser Val His Val
             20                  25                  30

Val Ala Arg Asp Leu Pro Glu Asp Thr Val Ala Gln Thr Phe Ala Ser
         35                  40                  45
```

Pro Trp Ala Gly Ala Ile Trp Asn Pro His Met Ser Lys Glu Asp Gly
    50                  55                  60

Pro Arg Gln Ala Lys Trp Glu Thr Ala Thr Phe Asn Gln Trp Val Asp
65                  70                  75                  80

Leu Val Pro Gln Gly Leu Ala Met Trp Leu Lys Gly Thr Arg Arg Tyr
                85                  90                  95

Ala Gln Asp Glu Ala Gly Leu Leu Gly His Trp Tyr Gln His Ile Thr
            100                 105                 110

Pro Asn Tyr Arg Lys Leu Glu Ser Ser Glu Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Glu Gly Gly Phe Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Val Lys Ser Asp Cys
        195                 200                 205

Lys Arg Cys Thr Ser Asp Ser Ser Asp Pro Asn Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Pro Thr Ile Asn Arg Ile Leu
                245                 250                 255

Gln His Cys Leu Arg Leu Asp Pro Ser Ile Ser Thr Asp Gly Thr Leu
            260                 265                 270

Glu Gly Ile Glu Ile Val Arg His Asn Val Gly Leu Arg Pro Ala Arg
        275                 280                 285

Arg Gly Gly Pro Arg Val Glu Val Glu Arg Val Ala Phe Pro Leu Glu
    290                 295                 300

Arg Gly Lys Ser Lys Leu Ser Leu Gly Thr Ala Arg Ala Asp Ser Ser
305                 310                 315                 320

Lys Pro Arg Arg Glu Val Pro Val Val His Ala Tyr Gly Phe Ser Ser
                325                 330                 335

Ala Gly Tyr Gln Gln Gly Trp Gly Ala Ala Leu Glu Val Ala Glu Leu
            340                 345                 350

Val Glu Gly Ala Ile Gly Ala Ala Pro Ala Arg Ser His Arg Trp
        355                 360                 365

Leu Ser Lys Leu
    370

<210> SEQ ID NO 62
<211> LENGTH: 372
<212> TYPE: PRT
<213> ORGANISM: Artificial Sequence
<220> FEATURE:
<223> OTHER INFORMATION: mutant DAAO

<400> SEQUENCE: 62

Met Ala Pro Ser Lys Arg Val Val Val Leu Gly Ser Gly Val Val Gly
1               5                   10                  15

Leu Ser Ser Ala Leu Thr Leu Ala Gln Lys Gly Tyr Ser Val His Val
            20                  25                  30

```
Val Ala Arg Asp Leu Pro Glu Asp Thr Val Ala Gln Thr Phe Ala Ser
         35                  40                  45

Pro Trp Ala Gly Ala Val Trp Asn Pro His Met Ser Lys Glu Asp Gly
 50                  55                  60

Pro Arg Gln Ala Lys Trp Glu Thr Ala Thr Phe Asn Gln Trp Val Asp
 65                  70                  75                  80

Leu Val Pro Gln Gly Leu Ala Met Trp Leu Lys Gly Thr Arg Arg Tyr
                 85                  90                  95

Ala Gln Asp Glu Ala Gly Leu Leu Gly His Trp Tyr Gln His Ile Thr
                100                 105                 110

Pro Asn Tyr Arg Lys Leu Glu Ser Glu Cys Pro Pro Gly Ala Ile
                115                 120                 125

Gly Val Thr Tyr Asp Thr Leu Ser Val Asn Ala Pro Lys Phe Cys Gln
        130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Glu Gly Phe Asp Leu Ile Val
                165                 170                 175

Asn Ala Thr Gly Leu Gly Ala Lys Ser Ile Ala Gly Val Glu Asp Gln
                180                 185                 190

Glu Val Glu Pro Ile Arg Gly Gln Thr Val Leu Val Lys Ser Asp Cys
                195                 200                 205

Lys Arg Cys Thr Ser Asp Ser Ser Asp Pro Asn Ser Pro Ala Tyr Ile
        210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Pro Thr Ile Asn Arg Ile Leu
                245                 250                 255

Gln His Cys Leu Arg Leu Asp Pro Ser Ile Ser Thr Asp Gly Thr Leu
                260                 265                 270

Glu Gly Ile Glu Ile Val Arg His Asn Val Gly Leu Arg Pro Ala Arg
                275                 280                 285

Arg Gly Gly Pro Arg Val Glu Val Glu Arg Val Ala Phe Pro Leu Glu
        290                 295                 300

Arg Gly Lys Ser Lys Leu Ser Leu Gly Thr Ala Arg Ala Asp Ser Ser
305                 310                 315                 320

Lys Pro Arg Arg Glu Val Pro Val Val His Ala Tyr Gly Phe Ser Ser
                325                 330                 335

Ala Gly Tyr Gln Gln Gly Trp Gly Ala Ala Leu Glu Val Ala Glu Leu
                340                 345                 350

Val Glu Gly Ala Ile Gly Ala Ala Pro Ala Arg Ser Ser His Arg Trp
        355                 360                 365

Leu Ser Lys Leu
    370

<210> SEQ ID NO 63
<211> LENGTH: 372
<212> TYPE: PRT
<213> ORGANISM: Artificial Sequence
<220> FEATURE:
<223> OTHER INFORMATION: mutant DAAO

<400> SEQUENCE: 63

Met Ala Pro Ser Lys Arg Val Val Val Leu Gly Ser Gly Val Val Gly
1               5                   10                  15
```

Leu Ser Ser Ala Leu Thr Leu Ala Gln Lys Gly Tyr Ser Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Asn Pro His Met Ser Lys Glu Asp Gly
    50                  55                  60

Pro Arg Gln Ala Lys Trp Glu Thr Ala Thr Phe Asn Gln Trp Val Asp
65                  70                  75                  80

Leu Val Pro Gln Gly Leu Ala Met Trp Leu Lys Gly Thr Arg Arg Tyr
                85                  90                  95

Ala Gln Asp Glu Ala Gly Leu Leu Gly His Trp Tyr Gln His Ile Thr
            100                 105                 110

Pro Asn Tyr Arg Lys Leu Glu Ser Ser Glu Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Glu Gly Gly Phe Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Val Lys Ser Asp Cys
        195                 200                 205

Lys Ala Cys Thr Ser Asp Ser Asp Pro Asn Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Pro Thr Ile Asn Arg Ile Leu
                245                 250                 255

Gln His Cys Leu Arg Leu Asp Pro Ser Ile Ser Thr Asp Gly Thr Leu
            260                 265                 270

Glu Gly Ile Glu Ile Val Arg His Asn Val Gly Leu Arg Pro Ala Arg
        275                 280                 285

Arg Gly Gly Pro Arg Val Glu Val Arg Val Ala Phe Pro Leu Glu
    290                 295                 300

Arg Gly Lys Ser Lys Leu Ser Leu Gly Thr Ala Arg Ala Asp Ser Ser
305                 310                 315                 320

Lys Pro Arg Arg Glu Val Pro Val Val His Ala Tyr Gly Phe Ser Ser
                325                 330                 335

Ala Gly Tyr Gln Gln Gly Trp Gly Ala Ala Leu Glu Val Ala Glu Leu
            340                 345                 350

Val Glu Gly Ala Ile Gly Ala Ala Pro Ala Arg Ser Ser His Arg Trp
        355                 360                 365

Leu Ser Lys Leu
    370

<210> SEQ ID NO 64
<211> LENGTH: 372
<212> TYPE: PRT
<213> ORGANISM: Artificial Sequence
<220> FEATURE:
<223> OTHER INFORMATION: mutant DAAO

<400> SEQUENCE: 64

```
Met Ala Pro Ser Lys Arg Val Val Leu Gly Ser Gly Val Gly
1               5                   10                  15

Leu Ser Ser Ala Leu Thr Leu Ala Gln Lys Gly Tyr Ser Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Asn Pro His Met Ser Lys Glu Asp Gly
    50                  55                  60

Pro Arg Gln Ala Lys Trp Glu Thr Ala Thr Phe Asn Gln Trp Val Asp
65              70                  75                  80

Leu Val Pro Gln Gly Leu Ala Met Trp Leu Lys Gly Thr Arg Arg Tyr
                85                  90                  95

Ala Gln Asp Glu Ala Gly Leu Leu Gly His Trp Tyr Gln His Ile Thr
                100                 105                 110

Pro Asn Tyr Arg Lys Leu Glu Ser Ser Glu Cys Pro Pro Gly Ala Ile
            115                 120                 125

Gly Val Thr Tyr Asp Thr Leu Ser Val Asn Ala Pro Lys Phe Cys Gln
130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Glu Gly Phe Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Val Lys Ser Asp Cys
            195                 200                 205

Lys Arg Cys Thr Ser Asp Ser Ser Asp Pro Asn Ser Arg Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Pro Thr Ile Asn Arg Ile Leu
            245                 250                 255

Gln His Cys Leu Arg Leu Asp Pro Ser Ile Ser Thr Asp Gly Thr Leu
            260                 265                 270

Glu Gly Ile Glu Ile Val Arg His Asn Val Gly Leu Arg Pro Ala Arg
            275                 280                 285

Arg Gly Gly Pro Arg Val Glu Val Arg Val Ala Phe Pro Leu Glu
290                 295                 300

Arg Gly Lys Ser Lys Leu Ser Leu Gly Thr Ala Arg Ala Asp Ser Ser
305                 310                 315                 320

Lys Pro Arg Arg Glu Val Pro Val His Ala Tyr Gly Phe Ser Ser
            325                 330                 335

Ala Gly Tyr Gln Gln Gly Trp Gly Ala Ala Leu Glu Val Ala Glu Leu
            340                 345                 350

Val Glu Gly Ala Ile Gly Ala Ala Pro Ala Arg Ser Ser His Arg Trp
            355                 360                 365

Leu Ser Lys Leu
    370

<210> SEQ ID NO 65
<211> LENGTH: 372
<212> TYPE: PRT
<213> ORGANISM: Artificial Sequence
<220> FEATURE:
```

<223> OTHER INFORMATION: mutant DAAO

<400> SEQUENCE: 65

Met Ala Pro Ser Lys Arg Val Val Val Leu Gly Ser Gly Val Val Gly
1               5                   10                  15

Leu Ser Ser Ala Leu Thr Leu Ala Gln Lys Gly Tyr Ser Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Asn Pro His Met Ser Lys Glu Asp Gly
    50                  55                  60

Pro Arg Gln Ala Lys Trp Glu Thr Ala Thr Phe Asn Gln Trp Val Asp
65                  70                  75                  80

Leu Val Pro Gln Gly Leu Ala Met Trp Leu Lys Gly Thr Arg Arg Tyr
                85                  90                  95

Ala Gln Asp Glu Ala Gly Leu Leu Gly His Trp Tyr Gln His Ile Thr
            100                 105                 110

Pro Asn Tyr Arg Lys Leu Glu Ser Ser Glu Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Glu Gly Phe Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Val Lys Ser Asp Cys
        195                 200                 205

Lys Ala Cys Thr Ser Asp Ser Ser Asp Pro Asn Ser Arg Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Pro Thr Ile Asn Arg Ile Leu
                245                 250                 255

Gln His Cys Leu Arg Leu Asp Pro Ser Ile Ser Thr Asp Gly Thr Leu
            260                 265                 270

Glu Gly Ile Glu Ile Val Arg His Asn Val Gly Leu Arg Pro Ala Arg
        275                 280                 285

Arg Gly Gly Pro Arg Val Glu Val Arg Val Ala Phe Pro Leu Glu
    290                 295                 300

Arg Gly Lys Ser Lys Leu Ser Leu Gly Thr Ala Arg Ala Asp Ser Ser
305                 310                 315                 320

Lys Pro Arg Arg Glu Val Pro Val His Ala Tyr Gly Phe Ser Ser
                325                 330                 335

Ala Gly Tyr Gln Gln Gly Trp Gly Ala Ala Leu Glu Val Ala Glu Leu
            340                 345                 350

Val Glu Gly Ala Ile Gly Ala Ala Pro Ala Arg Ser Ser His Arg Trp
        355                 360                 365

Leu Ser Lys Leu
    370

<210> SEQ ID NO 66
<211> LENGTH: 368

```
<212> TYPE: PRT
<213> ORGANISM: Artificial Sequence
<220> FEATURE:
<223> OTHER INFORMATION: mutant DAAO

<400> SEQUENCE: 66
```

| | | | | | | | | | | | | | | |
|---|---|---|---|---|---|---|---|---|---|---|---|---|---|---|
| Met | Gly | Ser | Gln | Lys | Arg | Val | Val | Leu | Gly | Ser | Gly | Val | Ile | Gly |
| 1 | | | | 5 | | | | | 10 | | | | | 15 |
| Leu | Ser | Ser | Ala | Leu | Ile | Leu | Ala | Arg | Lys | Gly | Tyr | Ser | Val | His | Ile |
| | | | 20 | | | | | 25 | | | | | 30 | | |
| Leu | Ala | Arg | Asp | Leu | Pro | Glu | Asp | Val | Ser | Ser | Gln | Thr | Phe | Ala | Ser |
| | | 35 | | | | | 40 | | | | | 45 | | | |
| Pro | Trp | Ala | Gly | Ala | Ile | Trp | Asn | Pro | His | Met | Thr | Leu | Thr | Asp | Gly |
| | 50 | | | | | 55 | | | | | 60 | | | | |
| Pro | Arg | Gln | Ala | Lys | Trp | Glu | Glu | Ser | Thr | Phe | Lys | Lys | Trp | Val | Glu |
| 65 | | | | | 70 | | | | | 75 | | | | | 80 |
| Leu | Val | Pro | Thr | Gly | His | Ala | Met | Trp | Leu | Lys | Gly | Thr | Arg | Arg | Phe |
| | | | | 85 | | | | | 90 | | | | | 95 | |
| Ala | Gln | Asn | Glu | Asp | Gly | Leu | Leu | Gly | His | Trp | Tyr | Lys | Asp | Ile | Thr |
| | | | 100 | | | | | 105 | | | | | 110 | | |
| Pro | Asn | Tyr | Arg | Pro | Leu | Pro | Ser | Ser | Glu | Cys | Pro | Pro | Gly | Ala | Ile |
| | | | 115 | | | | | 120 | | | | | 125 | | |
| Gly | Val | Thr | Tyr | Asp | Thr | Leu | Ser | Val | His | Ala | Pro | Lys | Tyr | Cys | Gln |
| | 130 | | | | | 135 | | | | | 140 | | | | |
| Tyr | Leu | Ala | Arg | Glu | Leu | Gln | Lys | Leu | Gly | Ala | Thr | Phe | Glu | Arg | Arg |
| 145 | | | | | 150 | | | | | 155 | | | | | 160 |
| Thr | Val | Thr | Ser | Leu | Glu | Gln | Ala | Phe | Asp | Gly | Ala | Asp | Leu | Val | Val |
| | | | | 165 | | | | | 170 | | | | | 175 | |
| Asn | Ala | Thr | Gly | Leu | Gly | Ala | Lys | Ser | Ile | Ala | Gly | Ile | Asp | Asp | Gln |
| | | | 180 | | | | | 185 | | | | | 190 | | |
| Ala | Ala | Glu | Pro | Ile | Arg | Gly | Gln | Thr | Val | Leu | Val | Lys | Ser | Pro | Cys |
| | | | 195 | | | | | 200 | | | | | 205 | | |
| Lys | Arg | Cys | Thr | Ser | Asp | Ser | Ser | Asp | Pro | Ala | Ser | Pro | Ala | Tyr | Ile |
| 210 | | | | | 215 | | | | | 220 | | | | | |
| Ile | Pro | Arg | Pro | Gly | Gly | Glu | Val | Ile | Cys | Gly | Gly | Thr | Tyr | Gly | Val |
| 225 | | | | | 230 | | | | | 235 | | | | | 240 |
| Gly | Asp | Trp | Asp | Leu | Ser | Val | Asn | Pro | Glu | Thr | Val | Gln | Arg | Ile | Leu |
| | | | | 245 | | | | | 250 | | | | | 255 | |
| Lys | His | Cys | Leu | Arg | Leu | Asp | Pro | Thr | Ile | Ser | Ser | Asp | Gly | Thr | Ile |
| | | | 260 | | | | | 265 | | | | | 270 | | |
| Glu | Gly | Ile | Glu | Val | Leu | Arg | His | Asn | Val | Gly | Leu | Arg | Pro | Ala | Arg |
| | | | 275 | | | | | 280 | | | | | 285 | | |
| Arg | Gly | Gly | Pro | Arg | Val | Glu | Ala | Glu | Arg | Ile | Val | Leu | Pro | Leu | Asp |
| | 290 | | | | | 295 | | | | | 300 | | | | |
| Arg | Thr | Lys | Ser | Pro | Leu | Ser | Leu | Gly | Arg | Gly | Ser | Ala | Arg | Ala | Ala |
| 305 | | | | | 310 | | | | | 315 | | | | | 320 |
| Lys | Glu | Lys | Glu | Val | Thr | Leu | Val | His | Ala | Tyr | Gly | Phe | Ser | Ser | Ala |
| | | | | 325 | | | | | 330 | | | | | 335 | |
| Gly | Tyr | Gln | Gln | Ser | Trp | Gly | Ala | Ala | Glu | Asp | Val | Ala | Gln | Leu | Val |
| | | | 340 | | | | | 345 | | | | | 350 | | |
| Asp | Glu | Ala | Phe | Gln | Arg | Tyr | His | Gly | Ala | Ala | Arg | Glu | Ser | Lys | Leu |
| | | | 355 | | | | | 360 | | | | | 365 | | |

```
<210> SEQ ID NO 67
<211> LENGTH: 368
```

```
<212> TYPE: PRT
<213> ORGANISM: Artificial Sequence
<220> FEATURE:
<223> OTHER INFORMATION: mutant DAAO

<400> SEQUENCE: 67

Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
            35                  40                  45

Pro Trp Ala Gly Ala Val Trp Asn Pro His Met Thr Leu Thr Asp Gly
50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Pro Gly Ala Ile
            115                 120                 125

Gly Val Thr Tyr Asp Thr Leu Ser Val His Ala Pro Lys Tyr Cys Gln
130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
            195                 200                 205

Lys Arg Cys Thr Ser Asp Ser Ser Asp Pro Ala Ser Pro Ala Tyr Ile
210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
            275                 280                 285

Arg Gly Gly Pro Arg Val Glu Ala Glu Arg Ile Val Leu Pro Leu Asp
290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
            355                 360                 365

<210> SEQ ID NO 68
<211> LENGTH: 368
```

<212> TYPE: PRT
<213> ORGANISM: Artificial Sequence
<220> FEATURE:
<223> OTHER INFORMATION: mutant DAAO

<400> SEQUENCE: 68

```
Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
                35                  40                  45

Pro Trp Ala Gly Ala Val Trp Thr Pro Gln Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Ala Cys Thr Ser Asp Ser Ser Asp Pro Ala Ser Pro Ala Tyr Ile
210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365
```

<210> SEQ ID NO 69
<211> LENGTH: 368

<212> TYPE: PRT
<213> ORGANISM: Artificial Sequence
<220> FEATURE:
<223> OTHER INFORMATION: mutant DAAO

<400> SEQUENCE: 69

```
Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
            35                  40                  45

Pro Trp Ala Gly Ala Val Trp Thr Pro Gln Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
                100                 105                 110

Pro Asn Tyr Arg Pro Leu Pro Ser Ser Glu Cys Pro Pro Gly Ala Ile
            115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
                180                 185                 190

Ala Ala Glu Pro Ile Arg Gly Gln Thr Val Leu Val Lys Ser Pro Cys
            195                 200                 205

Lys Arg Cys Thr Ser Asp Ser Ser Asp Pro Ala Ser Arg Ala Tyr Ile
    210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
                260                 265                 270

Glu Gly Ile Glu Val Leu Arg His Asn Val Gly Leu Arg Pro Ala Arg
            275                 280                 285

Arg Gly Gly Pro Arg Val Glu Ala Glu Arg Ile Val Leu Pro Leu Asp
    290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
                340                 345                 350

Asp Glu Ala Phe Gln Arg Tyr His Gly Ala Ala Arg Glu Ser Lys Leu
            355                 360                 365
```

<210> SEQ ID NO 70
<211> LENGTH: 368

<212> TYPE: PRT
<213> ORGANISM: Artificial Sequence
<220> FEATURE:
<223> OTHER INFORMATION: mutant DAAO

<400> SEQUENCE: 70

```
Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
            35                  40                  45

Pro Trp Ala Gly Ala Val Trp Thr Pro Gln Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Ala Cys Thr Ser Asp Ser Ser Asp Pro Ala Ser Arg Ala Tyr Ile
210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365
```

<210> SEQ ID NO 71
<211> LENGTH: 368

<212> TYPE: PRT
<213> ORGANISM: Artificial Sequence
<220> FEATURE:
<223> OTHER INFORMATION: mutant DAAO

<400> SEQUENCE: 71

```
Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Val Trp Asn Pro His Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Ala Cys Thr Ser Asp Ser Ser Asp Pro Ala Ser Pro Ala Tyr Ile
    210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
    290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365
```

<210> SEQ ID NO 72
<211> LENGTH: 368

<212> TYPE: PRT
<213> ORGANISM: Artificial Sequence
<220> FEATURE:
<223> OTHER INFORMATION: mutant DAAO

<400> SEQUENCE: 72

```
Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
            35                  40                  45

Pro Trp Ala Gly Ala Val Trp Asn Pro His Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Pro Gly Ala Ile
    115                 120                 125

Gly Val Thr Tyr Asp Thr Leu Ser Val His Ala Pro Lys Tyr Cys Gln
130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
    195                 200                 205

Lys Arg Cys Thr Ser Asp Ser Ser Asp Pro Ala Ser Arg Ala Tyr Ile
210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
    275                 280                 285

Arg Gly Gly Pro Arg Val Glu Ala Glu Arg Ile Val Leu Pro Leu Asp
290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
    355                 360                 365
```

<210> SEQ ID NO 73
<211> LENGTH: 368

<212> TYPE: PRT
<213> ORGANISM: Artificial Sequence
<220> FEATURE:
<223> OTHER INFORMATION: mutant DAAO

<400> SEQUENCE: 73

```
Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
                35                  40                  45

Pro Trp Ala Gly Ala Val Trp Asn Pro His Met Thr Leu Thr Asp Gly
50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
                100                 105                 110

Pro Asn Tyr Arg Pro Leu Pro Ser Ser Glu Cys Pro Pro Gly Ala Ile
                115                 120                 125

Gly Val Thr Tyr Asp Thr Leu Ser Val His Ala Pro Lys Tyr Cys Gln
130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
                180                 185                 190

Ala Ala Glu Pro Ile Arg Gly Gln Thr Val Leu Val Lys Ser Pro Cys
                195                 200                 205

Lys Ala Cys Thr Ser Asp Ser Ser Asp Pro Ala Ser Arg Ala Tyr Ile
210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
                260                 265                 270

Glu Gly Ile Glu Val Leu Arg His Asn Val Gly Leu Arg Pro Ala Arg
                275                 280                 285

Arg Gly Gly Pro Arg Val Glu Ala Glu Arg Ile Val Leu Pro Leu Asp
290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
                340                 345                 350

Asp Glu Ala Phe Gln Arg Tyr His Gly Ala Ala Arg Glu Ser Lys Leu
                355                 360                 365
```

<210> SEQ ID NO 74
<211> LENGTH: 368

<212> TYPE: PRT
<213> ORGANISM: Artificial Sequence
<220> FEATURE:
<223> OTHER INFORMATION: mutant DAAO

<400> SEQUENCE: 74

```
Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
                35                  40                  45

Pro Trp Ala Gly Ala Ile Trp Asn Pro His Met Thr Leu Thr Asp Gly
50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                    85                  90                  95

Ala Gln Asn Glu Asp Gly Leu Leu Gly His Trp Tyr Lys Asp Ile Thr
                100                 105                 110

Pro Asn Tyr Arg Pro Leu Pro Ser Ser Glu Cys Pro Pro Gly Ala Ile
            115                 120                 125

Gly Val Thr Tyr Asp Thr Leu Ser Val His Ala Pro Lys Tyr Cys Gln
        130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                    165                 170                 175

Asn Ala Thr Gly Leu Gly Ala Lys Ser Ile Ala Gly Ile Asp Asp Gln
                180                 185                 190

Ala Ala Glu Pro Ile Arg Gly Gln Thr Val Leu Val Lys Ser Pro Cys
            195                 200                 205

Lys Ala Cys Thr Ser Asp Ser Ser Asp Pro Ala Ser Pro Ala Tyr Ile
        210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                    245                 250                 255

Lys His Cys Leu Arg Leu Asp Pro Thr Ile Ser Ser Asp Gly Thr Ile
                260                 265                 270

Glu Gly Ile Glu Val Leu Arg His Asn Val Gly Leu Arg Pro Ala Arg
            275                 280                 285

Arg Gly Gly Pro Arg Val Glu Ala Glu Arg Ile Val Leu Pro Leu Asp
        290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                    325                 330                 335

Gly Tyr Gln Gln Ser Trp Gly Ala Ala Glu Asp Val Ala Gln Leu Val
                340                 345                 350

Asp Glu Ala Phe Gln Arg Tyr His Gly Ala Ala Arg Glu Ser Lys Leu
            355                 360                 365
```

<210> SEQ ID NO 75
<211> LENGTH: 368

<212> TYPE: PRT
<213> ORGANISM: Artificial Sequence
<220> FEATURE:
<223> OTHER INFORMATION: mutant DAAO

<400> SEQUENCE: 75

```
Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
            35                  40                  45

Pro Trp Ala Gly Ala Ile Trp Asn Pro His Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
                100                 105                 110

Pro Asn Tyr Arg Pro Leu Pro Ser Ser Glu Cys Pro Pro Gly Ala Ile
            115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
                180                 185                 190

Ala Ala Glu Pro Ile Arg Gly Gln Thr Val Leu Val Lys Ser Pro Cys
            195                 200                 205

Lys Arg Cys Thr Ser Asp Ser Ser Asp Pro Ala Ser Arg Ala Tyr Ile
    210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
                260                 265                 270

Glu Gly Ile Glu Val Leu Arg His Asn Val Gly Leu Arg Pro Ala Arg
            275                 280                 285

Arg Gly Gly Pro Arg Val Glu Ala Glu Arg Ile Val Leu Pro Leu Asp
    290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
                340                 345                 350

Asp Glu Ala Phe Gln Arg Tyr His Gly Ala Ala Arg Glu Ser Lys Leu
            355                 360                 365
```

<210> SEQ ID NO 76
<211> LENGTH: 368

<212> TYPE: PRT
<213> ORGANISM: Artificial Sequence
<220> FEATURE:
<223> OTHER INFORMATION: mutant DAAO

<400> SEQUENCE: 76

```
Met Gly Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
            35                  40                  45

Pro Trp Ala Gly Ala Ile Trp Asn Pro His Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Ala Cys Thr Ser Asp Ser Ser Asp Pro Ala Ser Arg Ala Tyr Ile
    210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
    290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365
```

<210> SEQ ID NO 77
<211> LENGTH: 372

```
<212> TYPE: PRT
<213> ORGANISM: Artificial Sequence
<220> FEATURE:
<223> OTHER INFORMATION: mutant DAAO

<400> SEQUENCE: 77
```

| | | | | | | | | | | | | | | |
|---|---|---|---|---|---|---|---|---|---|---|---|---|---|---|
| Met | Thr | Gln | Asn | Lys | Arg | Val | Val | Leu | Gly | Ser | Gly | Val | Ile | Gly |
| 1 | | | | 5 | | | | | 10 | | | | | 15 |
| Leu | Ser | Cys | Ala | Leu | Ala | Leu | Ala | Gln | Lys | Gly | Tyr | Lys | Val | His | Val |
| | | | 20 | | | | | 25 | | | | | 30 | | |
| Val | Ala | Arg | Asp | Leu | Pro | Glu | Asp | Thr | Val | Ala | Gln | Thr | Phe | Ala | Ser |
| | | 35 | | | | | 40 | | | | | 45 | | | |
| Pro | Trp | Ala | Gly | Ala | Val | Trp | Thr | Pro | Gln | Met | Ser | Lys | Glu | Ala | Gly |
| 50 | | | | | 55 | | | | | 60 | | | | | |
| Pro | Arg | Gln | Ala | Lys | Trp | Glu | Glu | Ala | Thr | Phe | Lys | Gln | Trp | Val | Asp |
| 65 | | | | 70 | | | | | 75 | | | | | 80 | |
| Phe | Val | Pro | Gln | Gly | Leu | Ala | Met | Trp | Leu | Lys | Gly | Thr | Arg | Arg | Phe |
| | | | | 85 | | | | | 90 | | | | | 95 | |
| Ala | Glu | Thr | Glu | Ala | Asp | Leu | Leu | Gly | His | Trp | Tyr | Lys | Asp | Ile | Val |
| | | | 100 | | | | | 105 | | | | | 110 | | |
| Pro | Asn | Tyr | Arg | His | Leu | Asn | Pro | Ser | Asp | Cys | Pro | Pro | Gly | Ala | Ile |
| | | | 115 | | | | | 120 | | | | | 125 | | |
| Gly | Val | Thr | Tyr | Asp | Thr | Leu | Ser | Val | Asn | Ala | Pro | Lys | Phe | Cys | Gln |
| | 130 | | | | | 135 | | | | | 140 | | | | |
| Tyr | Leu | Gln | Arg | Glu | Ala | Gln | Lys | Leu | Gly | Val | Thr | Phe | Glu | Arg | Arg |
| 145 | | | | | 150 | | | | | 155 | | | | | 160 |
| Leu | Val | Thr | Ser | Leu | Glu | Gln | Ile | Ala | Asp | Gly | Ala | Asp | Leu | Ile | Val |
| | | | | 165 | | | | | 170 | | | | | 175 | |
| Asn | Ala | Thr | Gly | Leu | Gly | Ala | Lys | Ser | Ile | Ala | Gly | Val | Glu | Asp | Gln |
| | | | 180 | | | | | 185 | | | | | 190 | | |
| Glu | Val | Glu | Pro | Ile | Arg | Gly | Gln | Thr | Val | Leu | Ile | Lys | Ser | Asn | Cys |
| | | | 195 | | | | | 200 | | | | | 205 | | |
| Lys | Arg | Cys | Thr | Ser | Asp | Ser | Ser | Asp | Pro | Lys | Ser | Pro | Ala | Tyr | Ile |
| | 210 | | | | | 215 | | | | | 220 | | | | |
| Ile | Pro | Arg | Pro | Gly | Gly | Glu | Val | Ile | Cys | Gly | Gly | Thr | Tyr | Leu | Val |
| 225 | | | | | 230 | | | | | 235 | | | | | 240 |
| Gly | Asn | Tyr | Asp | Leu | Ser | Val | Asp | Pro | Ala | Thr | Ile | Pro | Arg | Ile | Leu |
| | | | | 245 | | | | | 250 | | | | | 255 | |
| Lys | His | Cys | Leu | Arg | Leu | Asp | Pro | Ser | Ile | Ser | Thr | Asp | Gly | Thr | Leu |
| | | | 260 | | | | | 265 | | | | | 270 | | |
| Glu | Gly | Ile | Glu | Ile | Leu | Arg | His | Asn | Val | Gly | Leu | Arg | Pro | Ala | Arg |
| | | | 275 | | | | | 280 | | | | | 285 | | |
| Arg | Gly | Gly | Pro | Arg | Val | Glu | Leu | Glu | Arg | Val | Ser | Phe | Pro | Leu | Lys |
| | 290 | | | | | 295 | | | | | 300 | | | | |
| Arg | Gly | Gln | Ser | Leu | Leu | Ala | Leu | Gly | Thr | Ala | Lys | Ala | Ala | Glu | Gly |
| 305 | | | | | 310 | | | | | 315 | | | | | 320 |
| Lys | Ala | Ser | Arg | Thr | Val | Pro | Val | Val | His | Ala | Tyr | Gly | Phe | Ser | Ser |
| | | | | 325 | | | | | 330 | | | | | 335 | |
| Ala | Gly | Tyr | Gln | Gln | Gly | Trp | Gly | Ala | Ala | Leu | Glu | Val | Arg | Asp | Leu |
| | | | 340 | | | | | 345 | | | | | 350 | | |
| Val | Asp | Gln | Ala | Ile | Gly | Ser | Ser | Ser | Ala | Ser | Ser | Gly | Arg | Tyr |
| | | 355 | | | | | 360 | | | | | 365 | | |
| Leu | Ala | Lys | Leu |
| | 370 | | |

```
<210> SEQ ID NO 78
<211> LENGTH: 372
<212> TYPE: PRT
<213> ORGANISM: Artificial Sequence
<220> FEATURE:
<223> OTHER INFORMATION: mutant DAAO

<400> SEQUENCE: 78

Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
        20                  25                  30

Val Ala Arg Asp Leu Pro Glu Asp Thr Val Ala Gln Thr Phe Ala Ser
    35                  40                  45

Pro Trp Ala Gly Ala Val Trp Thr Pro Gln Met Ser Lys Glu Ala Gly
        50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Ala Cys Thr Ser Asp Ser Ser Asp Pro Lys Ser Pro Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365
```

```
Leu Ala Lys Leu
    370
```

<210> SEQ ID NO 79
<211> LENGTH: 372
<212> TYPE: PRT
<213> ORGANISM: Artificial Sequence
<220> FEATURE:
<223> OTHER INFORMATION: mutant DAAO

<400> SEQUENCE: 79

```
Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
            35                  40                  45

Pro Trp Ala Gly Ala Val Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Cys Thr Ser Asp Ser Ser Asp Pro Lys Ser Arg Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350
```

-continued

Val Asp Gln Ala Ile Gly Ser Ser Ser Ala Ser Ser Gly Arg Tyr
            355                 360                 365

Leu Ala Lys Leu
        370

<210> SEQ ID NO 80
<211> LENGTH: 372
<212> TYPE: PRT
<213> ORGANISM: Artificial Sequence
<220> FEATURE:
<223> OTHER INFORMATION: mutant DAAO

<400> SEQUENCE: 80

Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
                35                  40                  45

Pro Trp Ala Gly Ala Val Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
                100                 105                 110

Pro Asn Tyr Arg His Leu Asn Pro Ser Asp Cys Pro Pro Gly Ala Ile
                115                 120                 125

Gly Val Thr Tyr Asp Thr Leu Ser Val Asn Ala Pro Lys Phe Cys Gln
            130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
                180                 185                 190

Glu Val Glu Pro Ile Arg Gly Gln Thr Val Leu Ile Lys Ser Asn Cys
                195                 200                 205

Lys Ala Cys Thr Ser Asp Ser Ser Asp Pro Lys Ser Arg Ala Tyr Ile
                210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
                260                 265                 270

Glu Gly Ile Glu Ile Leu Arg His Asn Val Gly Leu Arg Pro Ala Arg
                275                 280                 285

Arg Gly Gly Pro Arg Val Glu Leu Glu Arg Val Ser Phe Pro Leu Lys
            290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
        370

<210> SEQ ID NO 81
<211> LENGTH: 372
<212> TYPE: PRT
<213> ORGANISM: Artificial Sequence
<220> FEATURE:
<223> OTHER INFORMATION: mutant DAAO

<400> SEQUENCE: 81

Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Ala Cys Thr Ser Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

```
Lys Ala Ser Arg Thr Val Pro Val Val His Ala Tyr Gly Phe Ser Ser
            325                 330                 335

Ala Gly Tyr Gln Gln Gly Trp Gly Ala Ala Leu Glu Val Arg Asp Leu
        340                 345                 350

Val Asp Gln Ala Ile Gly Ser Ser Ser Ala Ser Ser Gly Arg Tyr
        355                 360                 365

Leu Ala Lys Leu
        370

<210> SEQ ID NO 82
<211> LENGTH: 372
<212> TYPE: PRT
<213> ORGANISM: Artificial Sequence
<220> FEATURE:
<223> OTHER INFORMATION: mutant DAAO

<400> SEQUENCE: 82

Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
        50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Cys Thr Ser Asp Ser Ser Asp Pro Lys Ser Arg Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300
```

```
Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370
```

<210> SEQ ID NO 83
<211> LENGTH: 372
<212> TYPE: PRT
<213> ORGANISM: Artificial Sequence
<220> FEATURE:
<223> OTHER INFORMATION: mutant DAAO

<400> SEQUENCE: 83

```
Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
            35                  40                  45

Pro Trp Ala Gly Ala Val Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
            115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Ala Cys Thr Ser Asp Ser Ser Asp Pro Lys Ser Arg Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285
```

```
Arg Gly Gly Pro Arg Val Glu Leu Glu Arg Val Ser Phe Pro Leu Lys
            290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val His Ala Tyr Gly Phe Ser Ser
                325                 330                 335

Ala Gly Tyr Gln Gln Gly Trp Gly Ala Ala Leu Glu Val Arg Asp Leu
                340                 345                 350

Val Asp Gln Ala Ile Gly Ser Ser Ser Ala Ser Ser Gly Arg Tyr
                355                 360                 365

Leu Ala Lys Leu
    370

<210> SEQ ID NO 84
<211> LENGTH: 372
<212> TYPE: PRT
<213> ORGANISM: Artificial Sequence
<220> FEATURE:
<223> OTHER INFORMATION: mutant DAAO

<400> SEQUENCE: 84

Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
                35                  40                  45

Pro Trp Ala Gly Ala Ile Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
                100                 105                 110

Pro Asn Tyr Arg His Leu Asn Pro Ser Asp Cys Pro Pro Gly Ala Ile
                115                 120                 125

Gly Val Thr Tyr Asp Thr Leu Ser Val Asn Ala Pro Lys Phe Cys Gln
                130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
                180                 185                 190

Glu Val Glu Pro Ile Arg Gly Gln Thr Val Leu Ile Lys Ser Asn Cys
                195                 200                 205

Lys Ala Cys Thr Ser Asp Ser Ser Asp Pro Lys Ser Pro Ala Tyr Ile
                210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
                260                 265                 270
```

```
Glu Gly Ile Glu Ile Leu Arg His Asn Val Gly Leu Arg Pro Ala Arg
            275                 280                 285

Arg Gly Gly Pro Arg Val Glu Leu Glu Arg Val Ser Phe Pro Leu Lys
        290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
                355                 360                 365

Leu Ala Lys Leu
    370

<210> SEQ ID NO 85
<211> LENGTH: 372
<212> TYPE: PRT
<213> ORGANISM: Artificial Sequence
<220> FEATURE:
<223> OTHER INFORMATION: mutant DAAO

<400> SEQUENCE: 85

Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
            35                  40                  45

Pro Trp Ala Gly Ala Ile Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Cys Thr Ser Asp Ser Ser Asp Pro Lys Ser Arg Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255
```

```
Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
            355                 360                 365

Leu Ala Lys Leu
        370
```

<210> SEQ ID NO 86
<211> LENGTH: 372
<212> TYPE: PRT
<213> ORGANISM: Artificial Sequence
<220> FEATURE:
<223> OTHER INFORMATION: mutant DAAO

<400> SEQUENCE: 86

```
Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
            35                  40                  45

Pro Trp Ala Gly Ala Ile Trp Asn Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Ala Cys Thr Ser Asp Ser Ser Asp Pro Lys Ser Arg Ala Tyr Ile
    210                 215                 220

Ile Pro Arg Pro Gly Gly Glu Val Ile Cys Gly Gly Thr Tyr Leu Val
225                 230                 235                 240
```

-continued

```
Gly Asn Tyr Asp Leu Ser Val Asp Pro Ala Thr Ile Pro Arg Ile Leu
            245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
            275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ser Ala Ser Ser Gly Arg Tyr
            355                 360                 365

Leu Ala Lys Leu
    370
```

MODIFIED DAAO ENZYME AND APPLICATION THEREOF

PRIOR APPLICATIONS

This application is a continuation of International Application No. PCT/CN2020/134540, filed Dec. 8, 2020, which claims priority to CN201911249924.4, filed on Dec. 9, 2019. The contents of both applications are incorporated herein by reference in their entirety.

SEQUENCE LISTING

The instant application contains a Sequence Listing which has been submitted in ASCII format via EFS-Web and is hereby incorporated by reference in its entirety. The ASCII copy of the Sequence Listing, which was created on May 25, 2022, is named TC663.txt and is 274 kilobytes in size

TECHNICAL FIELD

The present invention relates to the field of enzyme engineering. In particular, the present invention refers to the modified D-amino acid oxidase (DAAO), and the use thereof in the production of glufosinate.

BACKGROUND

Glufosinate (also referred to as 4-[Hydroxy(methyl)phosphono]-D,L-homoalanine) is a herbicide in the second place in the world sales ranking, to which the transgenic crops are tolerant. Glufosinate is a broad-spectrum contact-killing herbicide that results in a disturbance in nitrogen metabolism in a plant by inhibiting the activity of L-glutamine synthetase, and eventually kills the plant. Glufosinate has significant advantages over glyphosate, such as the broad application, rapid effect, long duration, low toxicity, safety, etc. Therefore, the sales of glufosinate are increasing quickly, and there will be a great need thereof in the next period, and an excellent prospect.

However, the process for producing glufosinate is complex, resulting in a high difficulty in the production. The high price prevents it from rapidly replacing glyphosate. Currently, the commercial glufosinate is a racemic mixture comprising equal amounts of two optical isomers (D,L-glufosinate), in which only L-glufosinate is biologically active. Therefore, the preparation of chiral pure L-glufosinate by deracemization of D,L-glufosinate is practically important and becomes popular in the synthesis of L-glufosinate in recent years.

In recent years, many methods have been reported for preparing L-glufosinate from D,L-glufosinate. The traditional resolution method by chemical modification is not competitive due to the high cost and the fact that D-glufosinate cannot be used. Currently, the prime and representative technical routes for converting D-glufosinate-ammonium into L-glufosinate, which have been reported, are as follows.

1. D,L-glufosinate is converted into N-acetyl glufosinate, and then, L-glufosinate is obtained by the selective hydrolysis of L-N-acetyl glufosinate, which is catalyzed by carboxypeptidase, while D-N-Acetyl glufosinate cannot be hydrolyzed, and can be recycled into the hydrolysis step after chemical or enzymatic racemization (see, e.g., CN108690854A). The drawbacks of this method include the multiple steps of reactions, and the need of the separation of L-glufosinate, which is obtained from the hydrolysis, from the N-acetylated substrate.

2. D-Glufosinate is oxidized into 2-carbonyl-4-(hydroxymethylphosphono)butyric acid (PPO), and then, PPO is reduced or transaminated to generate L-Glufosinate-ammonium. In most of the references, D-amino acid oxidase (DAAO) is used to catalyze the oxidation of D-glufosinate into PPO, in which catalase (CAT) is usually added to remove the generated hydrogen peroxide. PPO can be reduced by formic acid under the catalysis of palladium on carbon to generate D,L-glufosinate, so that D,L-glufosinate can be gradually converted into L-glufosinate due to the stereoselectivity of DAAO (see, e.g., CN105567780A). The drawbacks of this solution include that a great amount of palladium-carbon catalyst is needed, and the raw materials for the reaction (such as oxygen and ammonium formate) will be wasted.

PPO can also be converted into L-glufosinate by the stereoselective transamination reaction catalyzed by L-amino acid transaminase (L-TA) (see, e.g., US20180030487A1). This solution has a drawback that the transamination step is a balanced reaction, and thus, it is needed to provide an excess amount of amino donor (amino acid or organic amine) to achieve a high conversion rate (for example, a conversion rate of 90% when providing 3 equivalents of the amino donor), and the excess amount of amino donor and the corresponding by-products will seriously influence the subsequent separation and purification steps.

In addition, PPO can be converted into L-glufosinate via the stereoselective reduction reaction catalyzed by L-amino acid dehydrogenase (L-AADH) (see, e.g., CN107502647A, CN109576236A, and CN109609582A). In this solution, the concentration of the converted substrate is low, or the loss is great.

The solution employing D-amino acid oxidase and L-amino acid dehydrogenase has potential cost advantages as compared to the above-mentioned solutions. However, in the methods that have been currently reported, the concentration of the substrate that can be converted is generally not high, or the loss is too great, resulting in excessive production costs. It is the choke point of the current processes to achieve the deracemization of a high concentration of D,L-glufosinate.

The main factor hindering the conversion of higher concentrations of substrates may include that: the recombinant DAAO enzyme is poor in stability and is unstable under the conditions of the reactor, and the enzyme is inactivated during the reaction.

Another limiting factor is the selective catalytic activity of the enzyme on D-glufosinate. Some modifications in DAAO have been conducted to confer the activity on D-glufosinate in the prior art.

In U.S. Pat. No. 7,939,709, mutants of DAAO from *Rhodotorula toruloides* (also known as *Rhodotorula gracilis*, see https://www.atcc.org/products/all/10788.aspx) were used for the purpose of synthesizing PPO from D-glufosinate. The mutants of DAAO from *Rhodotorula toruloides* as mentioned in the patent comprise a mutation F58K, a mutation at position M213 which is substituted with H, S, T, C, Q, G, N, and A, and mutations at positions 223 and 238. Tim Hawks et al. 2011 (D-glufosinate as a male sterility agent for hybrid seed production, *Plant Biotechnology Journal*, (2011) 9, pp. 301-314) reported the content similar to the above patent, in which the DAAO is from *Rhodotorula toruloides*, and comprises mutations at positions 58 and 213.

In U.S. Pat. No. 9,834,802, a mutant of DAAO from *Rhodotorula toruloides* and a transaminase (TA) were used to synthesize L-glufosinate from D,L-glufosinate. It is also described that the DAAO comprises one or more mutations at positions 54, 56, 58, 213, and 238, and several specific combinations are exemplified.

In CN109576236A, a mutant capable of oxidizing D-glufosinate was also constructed based on DAAO from *Rhodotorula toruloides*. The mutant has one or more mutations at amino acid positions 52, 54, 58, 213, and 335.

In other patent applications such as CN105567780A, CN109609582A, the oxidation of D-glufosinate with DAAO was also involved, but the sequence of the enzyme as used was not shown.

However, there is still a need of DAAOs that have higher stability and/or higher activity on D-glufosinate.

SUMMARY OF THE INVENTION

In the first aspect, the present invention provides a modified D-amino acid oxidase (DAAO), comprising, compared with its wild-type DAAO, amino acid substitutions at 4, 5, 6, 7, 8, 9, 10, 11, 12, 13, 14, 15, 16, 17, 18, 19, 20 or more positions, wherein the modified DAAO has the activity of catalyzing the oxidation of D-glufosinate into PPO.

In some embodiments, the modified DAAO comprises amino acid substitutions at positions 54, 56, 58 and 213, and the positions are numbered by reference to SEQ ID NO: 2. Preferably, the amino acid at position 54 is substituted by I, V, T or L, and more preferably I or V. Preferably, the amino acid at position 56 is substituted by N. Preferably, the amino acid at position 58 is substituted by H or Q, more preferably H. Preferably, the amino acid at position 213 is substituted by S or T, more preferably S. In some embodiments, the modified DAAO further comprises amino acid substitution(s) at position(s) 210 and/or 221. Preferably, the amino acid at position 210 is substituted by A, G or P, more preferably A. Preferably, the amino acid at position 221 is substituted by R.

In some embodiments, the modified DAAO comprises amino acid substitutions at positions 54, 58, 213 and 221, and the positions are numbered by reference to SEQ ID NO: 2. Preferably, the amino acid at position 54 is substituted by V, the amino acid at position 58 is substituted by Q, the amino acid at position 213 is substituted by S, and the amino acid at position 221 is substituted by R. In some embodiments, the modified DAAO further comprises amino acid substitution(s) at position(s) 210 and/or 56. Preferably, the amino acid at position 56 is substituted by N, and the amino acid at position 210 is substituted by A.

In some embodiments, the modified DAAO of the present invention further comprises amino acid substitutions at one or more positions selected from the group consisting of 2, 81, 97, 193, 194, 237, 265, 273, 274, 300, 317, 319, 337 and 342. Preferably, the amino acid at position 2 is substituted by C or S, the amino acid at position 81 is substituted by Y, the amino acid at position 97 is substituted by V, the amino acid at position 193 is substituted by T, the amino acid at position 194 is substituted by V or C, the amino acid at position 237 is substituted by V, the amino acid at position 265 is substituted by C, the amino acid at position 273 is substituted by D, the amino acid at position 274 is substituted by E, the amino acid at position 300 is substituted by S or T, the amino acid at position 317 is substituted by Y or W, the amino acid at position 319 is substituted by K, the amino acid at position 337 is substituted by S, and the amino acid at position 342 is substituted by S or H.

Alternatively, in some embodiments, the modified DAAO of the present invention further comprises amino acid substitutions at one or more positions selected from the group consisting of 194, 237, 265, 273, 274, 300, 317 and 319. Preferably, the amino acid at position 194 is substituted by V or C, the amino acid at position 237 is substituted by V, the amino acid at position 265 is substituted by C, the amino acid at position 273 is substituted by D, the amino acid at position 274 is substituted by E, the amino acid at position 300 is substituted by S, the amino acid at position 317 is substituted by Y or W, and the amino acid at position 319 is substituted by K.

Alternatively, in some embodiments, the modified DAAO of the present invention further comprises amino acid substitutions at one or more positions selected from the group consisting of 2, 81, 97, 193, 300, 337 and 342, wherein the amino acid at position 2 is substituted by C or S, the amino acid at position 81 is substituted by Y, the amino acid at position 97 is substituted by V, the amino acid at position 193 is substituted by T, the amino acid at position 300 is substituted by T, the amino acid at position 337 is substituted by S, and the amino acid at position 342 is substituted by S.

In some embodiments, the modified DAAO comprises amino acid substitutions at positions 54, 58, 194 and 213 as compared to SEQ ID NO: 1, wherein the modified DAAO has the activity of catalyzing the oxidation of D-glufosinate into PPO. Preferably, the amino acid at position 54 is substituted by I, V, T or L, the amino acid at position 58 is substituted by H or Q, the amino acid at position 194 is substituted by V or C, and the amino acid at position 213 is substituted by S or T. In some embodiments, the modified DAAO further comprises amino acid substitutions at one or more positions selected from the group consisting of positions 56, 210, 221, 237, 265, 273, 274, 300, 317 and 319. Preferably, the amino acid at position 56 is substituted by N, the amino acid at position 210 is substituted by A, G or P, the amino acid at position 221 is substituted by R, the amino acid at position 237 is substituted by V, the amino acid at position 265 is substituted by C, the amino acid at position 273 is substituted by D, the amino acid at position 274 is substituted by E, the amino acid at position 300 is substituted by S, the amino acid at position 317 is substituted by Y or W, and the amino acid at position 319 is substituted by K.

In some embodiments, the modified DAAO comprises or consists of the amino acid sequence of one of SEQ ID NOs: 5-86, or the modified DAAO comprises an amino acid sequence comprising 1-10 amino acid substitutions at positions other than positions 54, 56, 58, 194, 210, 213, 221, 237, 265, 273, 274, 300, 317 and 319 as compared to one of SEQ ID NOs: 5-30 and 66-76, comprising 1-10 amino acid substitutions at positions other than positions 2, 54, 56, 58, 81, 97, 193, 210, 213, 221, 300, 337 and 342 as compared to one of SEQ ID NOs: 31-57 and 77-86, or comprising 1-10 amino acid substitutions at positions other than positions 54, 56, 58, 210, 213 and 221 as compared to one of SEQ ID NOs: 58-65, wherein the modified DAAO has the activity of catalyzing the oxidation of D-glufosinate into PPO.

In the second aspect, the present invention provides a polynucleotide encoding the modified DAAO of the present invention, and a vector comprising the polynucleotide of the present invention.

In the third aspect, the present invention provides a host cell comprising the modified DAAO of the present invention, its coding polynucleotide, or a vector comprising the polynucleotide.

In the fourth aspect, the present invention provides a method of producing L-glufosinate, comprising contacting the modified DAAO of the present invention or the host cell of the present invention with D-glufosinate.

DETAILED DESCRIPTION OF THE INVENTION

The present invention mainly refers to a modified DAAO for catalyzing the oxidation of D-glufosinate to produce L-glufosinate. Unless otherwise specified, the terms used herein have the meaning generally understood by those skilled in the art.

I. Modified D-Amino Acid Oxidase

As used herein, the terms "D-amino acid oxidase" and "DAAO" refer to the enzyme catalyzing the oxidation of D-amino acid to generate keto acid (EC 1.4.3.3). Generally, a naturally occurring DAAO is not capable of catalyzing the oxidation of D-glufosinate. Therefore, the present invention provides a modified DAAO capable of catalyzing the oxidation of D-glufosinate into PPO. Preferably, the modified DAAO polypeptide has increased stability and/or increased activity of catalyzing the oxidation of D-glufosinate into PPO.

As used herein, the term "peptide" means a chain comprising at least two amino acids linked by peptide bond. The term "polypeptide" can be exchanged with "protein", and means a chain comprising ten or more amino acid residues. The chemical formulas or sequences of all the peptides and polypeptide herein are written in left-to-right order, showing the direction from the amino terminal to the carboxyl terminal.

The term "amino acid" includes amino acids naturally occurred in proteins and the unnatural amino acids. The conventional nomenclature (one-letter and three-letter) of the amino acids naturally occurred in proteins is employed, which can be seen in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989).

| Amino acid | One-letter | Three-letter |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tryosine | Y | Tyr |
| Valine | V | Val |

As used herein, the term "modification" refers to any chemical modification to the polypeptide, for example, the substitution, deletion, insertion and/or addition of amino acid(s).

In some embodiments, the modified DAAO of the present invention comprises 4, 5, 6, 7, 8, 9, 10, 11, 12, 13, 14, 15, 16, 17, 18, 19, 20 or more amino acid substitutions as compared to its wild-type DAAO, wherein the modified DAAO has the activity of catalyzing the oxidation of D-glufosinate into PPO. In some embodiments, the modified DAAO comprises amino acid substitutions at positions 54, 56, 58 and 213 as compared to its wild-type DAAO, and the positions are numbered by reference to SEQ ID NO: 2. Preferably, the amino acid at position 54 is substituted by I, V, T or L, and more preferably I or V. Preferably, the amino acid at position 56 is substituted by N. Preferably, the amino acid at position 58 is substituted by H or Q, more preferably H. Preferably, the amino acid at position 213 is substituted by S or T, more preferably S. In some embodiments, the modified DAAO comprises a combination of substitutions 54V, 56N, 58H and 213S, or 54I, 56N, 58H and 213S as compared to its wild-type DAAO. In some embodiments, the modified DAAO further comprises amino acid substitution(s) at position(s) 210 and/or 221. Preferably, the amino acid at position 210 is substituted by A, G or P, more preferably A. Preferably, the amino acid at position 221 is substituted by R.

In some embodiments, the modified DAAO comprises amino acid substitutions at positions 54, 58, 213 and 221, and the positions are numbered by reference to SEQ ID NO: 2. Preferably, the amino acid at position 54 is substituted by V, the amino acid at position 58 is substituted by Q, the amino acid at position 213 is substituted by S, and the amino acid at position 221 is substituted by R. In some embodiments, the modified DAAO further comprises amino acid substitution(s) at position(s) 210 and/or 56. Preferably, the amino acid at position 56 is substituted by N, and the amino acid at position 210 is substituted by A.

In some embodiments, the modified DAAO of the present invention further comprises amino acid substitutions at one or more positions selected from the group consisting of 2, 81, 97, 193, 194, 237, 265, 273, 274, 300, 317, 319, 337 and 342, and the positions are numbered by reference to SEQ ID NO: 2, wherein the modified DAAO has the activity of catalyzing the oxidation of D-glufosinate into PPO. Preferably, the amino acid at position 2 is substituted by C or S, the amino acid at position 81 is substituted by Y, the amino acid at position 97 is substituted by V, the amino acid at position 193 is substituted by T, the amino acid at position 194 is substituted by V or C, the amino acid at position 237 is substituted by V, the amino acid at position 265 is substituted by C, the amino acid at position 273 is substituted by D, the amino acid at position 274 is substituted by E, the amino acid at position 300 is substituted by S or T, the amino acid at position 317 is substituted by Y or W, the amino acid at position 319 is substituted by K, the amino acid at position 337 is substituted by S, and the amino acid at position 342 is substituted by S or H.

Alternatively, the modified DAAO of the present invention further comprises amino acid substitutions at one or more positions selected from the group consisting of 194, 237, 265, 273, 274, 300, 317 and 319, and the positions are numbered by reference to SEQ ID NO: 2, wherein the modified DAAO has the activity of catalyzing the oxidation of D-glufosinate into PPO. Preferably, the amino acid at position 194 is substituted by V or C, the amino acid at position 237 is substituted by V, the amino acid at position 265 is substituted by C, the amino acid at position 273 is substituted by D, the amino acid at position 274 is substituted by E, the amino acid at position 300 is substituted by S, the amino acid at position 317 is substituted by Y or W, and the amino acid at position 319 is substituted by K.

Alternatively, the modified DAAO of the present invention further comprises amino acid substitutions at one or more positions selected from the group consisting of 2, 81, 97, 193, 300, 337 and 342, and the positions are numbered by reference to SEQ ID NO: 2, wherein the modified DAAO has the activity of catalyzing the oxidation of D-glufosinate into PPO. Preferably, the amino acid at position 2 is substituted by C or S, the amino acid at position 81 is substituted by Y, the amino acid at position 97 is substituted by V, the amino acid at position 193 is substituted by T, the amino acid at position 300 is substituted by T, the amino acid at position 337 is substituted by S, and the amino acid at position 342 is substituted by S.

In some embodiments, the modified DAAO of the present invention comprises amino acid substitutions at positions 54, 58, 194 and 213 as compared to SEQ ID NO: 1, wherein the modified DAAO has the activity of catalyzing the oxidation of D-glufosinate into PPO. Preferably, the amino acid at position 54 is substituted by I, V, T or L, the amino acid at position 58 is substituted by H or Q, the amino acid at position 194 is substituted by V or C, and the amino acid at position 213 is substituted by S or T. In some embodiments, the modified DAAO further comprises amino acid substitutions at one or more positions selected from the group consisting of positions 56, 210, 221, 237, 265, 273, 274, 300, 317 and 319. Preferably, the amino acid at position 56 is substituted by N, the amino acid at position 210 is substituted by A, G or P, the amino acid at position 221 is substituted by R, the amino acid at position 237 is substituted by V, the amino acid at position 265 is substituted by C, the amino acid at position 273 is substituted by D, the amino acid at position 274 is substituted by E, the amino acid at position 300 is substituted by S, the amino acid at position 317 is substituted by Y or W, and the amino acid at position 319 is substituted by K. In some embodiments, the modified DAAO of the present invention further comprises conserved substitutions of one or more amino acids, or insertion of deletion of one or more amino acids as compared to SEQ ID NO: 1.

In some embodiments, the modified DAAO of the present invention comprises, as compared to its wild-type, a combination of amino acid substitutions selected from a group consisting of (the positions are numbered by reference to SEQ ID NO: 2):

54V, 58Q, 194V, 213S;
54V, 58Q, 194C, 213S;
54V, 58Q, 213S, 273D;
54V, 58Q, 213S, 317Y;
54V, 58Q, 213S, 317W;
54V, 58Q, 213S, 274E;
54V, 58Q, 213S, 319K;
54V, 58Q, 194C, 213S, 317Y;
54V, 58Q, 194C, 213S, 265C, 317Y;
54V, 58Q, 194C, 213S, 265C, 300S, 317Y;
54V, 58Q, 194C, 213T, 265C, 300S, 317Y;
54V, 58Q, 194C, 213S, 210G, 265C, 300S, 317Y;
54V, 58Q, 194C, 213S, 210P, 265C, 300S, 317Y;
54V, 58Q, 194C, 213S, 210A, 265C, 300S, 317Y;
54V, 58Q, 194C, 213S, 221R, 265C, 300S, 317Y;
54V, 58Q, 194C, 213S, 237A, 265C, 300S, 317Y;
54V, 58Q, 194C, 213S, 237V, 265C, 300S, 317Y;
54V, 56N, 58Q, 194C, 213S, 265C, 300S, 317Y;
54T, 56N, 58Q, 194C, 213S, 265C, 300S, 317Y;
54I, 56N, 58Q, 194C, 213S, 265C, 300S, 317Y;
54V, 56N, 58H, 194C, 213S, 265C, 300S, 317Y;
54L, 56N, 58Q, 194C, 213S, 265C, 300S, 317Y;
54I, 56N, 58H, 194C, 213S, 265C, 300S, 317Y;
54V, 56N, 58H, 194C, 213S, 237V, 265C, 300S, 317Y;
54V, 56N, 58H, 194C, 213S, 210A, 237V, 265C, 300S, 317Y;
54I, 56N, 58H, 194C, 213S, 210A, 221R, 265C, 300S, 317Y;
54L, 56N, 58Q;
54T, 56N, 58Q;
54I, 56N, 58H;
54V, 56N, 58H;
54L, 56N, 58Q, 213S;
54T, 56N, 58Q, 213S;
54I, 56N, 58H, 213S;
54V, 56N, 58H, 213S;
2C, 54V, 56N, 58H, 213S;
2S, 54V, 56N, 58H, 213S;
54V, 56N, 58H, 81Y, 213S;
54V, 56N, 58H, 97V, 213S;
54V, 56N, 58H, 193T, 213S;
54V, 56N, 58H, 213S, 300T;
54V, 56N, 58H, 213S, 337S;
54V, 56N, 58H, 213S, 342S;
2S, 54V, 56N, 58H, 81Y, 97V, 193T, 213S, 337S;
54V, 56N, 58H, 97V, 193A, 213S, 337S, 342H;
2C, 54V, 56N, 58H, 81Y, 97V, 213S, 337S;
2C, 54V, 56N, 58H, 81Y, 97V, 193A, 213S, 342S;
54V, 56N, 58H, 97V, 193T, 213S, 337S, 342H;
54V, 56N, 58H, 81Y, 97V, 193T, 213S, 337S, 342H;
54V, 56N, 58H, 97V, 193T, 213S, 300T, 337S, 342H;
54V, 56N, 58H, 81Y, 97V, 193T, 213S, 300T, 337S, 342H;
54V, 56N, 58H, 97V, 193T, 210A, 213S, 300T, 337S, 342H;
54V, 56N, 58H, 97V, 193T, 213S, 221R, 300T, 337S, 342H;
54V, 56N, 58H, 97V, 193T, 210A, 213S, 221R, 300T, 337S, 342H;
58K, 213T;
54V, 56N, 58H, 210A, 213S;
54V, 56N, 58H, 213S, 221R;
54V, 56N, 58H, 210A, 213S, 221R;
54I, 56N, 58H, 210A, 213S;
54I, 56N, 58H, 213S, 221R;
54I, 56N, 58H, 210A, 213S, 221R;
54V, 58Q, 213S;
54V, 58Q, 210A, 213S;
54V, 58Q, 213S, 221R; and
54V, 58Q, 210A, 213S, 221R.

The DAAO polypeptide, based on which the modification of amino acid is conducted, is referred to as the initiate DAAO herein. The initiate DAAO may be a wild-type DAAO, and may also be a variant of wild-type DAAO. For example, if the modification is initiated based on the polypeptide of SEQ ID NO: 1, the polypeptide of SEQ ID NO: 1 is the "initiate DAAO" with respect to the modified DAAO; and if the modification is initiated based on a variant polypeptide of SEQ ID NO: 1 (e.g., SEQ ID NOs: 4-30), the variant polypeptide is the"initiate DAAO" with respect to the modified DAAO.

As used herein, the term "wild-type DAAO" refers to the naturally occurring DAAO. In some embodiments, the wild-type DAAO is the DAAO from the genus of *Rhodotorula*. In some embodiments, the wild-type DAAO is one of SEQ ID NOs: 1-3. SEQ ID NO: 1 is the amino acid sequence of the DAAO from *Rhodotorula toruloides* (GenBank Assesion No. CAJ87425.1), SEQ ID NO: 2 is the amino acid sequence of the DAAO from *Rhodotorula* sp. JG-1b (GenBank Assesion No. KWU45700.1), and SEQ ID NO: 3 is the amino acid sequence of the putative DAAO from *Rhodotorula taiwanensis* (GenBank Assesion No. POY70719.1).

For the present invention, in order to determine the percentage identity between two amino acid sequences or two nucleic acid sequences, the sequences are aligned for the purpose of optimal comparison (e.g., a gap can be introduced into the first amino acid or nucleic acid sequence for the optimal alignment with the second amino acid or nucleic acid sequence). Then, the amino acid residues or nucleotides at the corresponding amino acid positions or nucleotide positions are compared. When a position in the first sequence is occupied by the same amino acid residue or nucleotide at the corresponding position in the second sequence, these molecules are identical at this position. The percentage identity between two sequences is a function of the number of identical positions shared by the sequences (i.e., percentage identity=number of identical positions/total number of positions (i.e., the overlapping positions)×100). Preferably, the two sequences are identical in length.

A person skilled in the art knows that various computer programs can be used to determine the identity between two sequences.

"Amino acid identity percentage" or "amino acid sequence identity percentage" refers to the comparison between the amino acids of two polypeptides, and when optimally aligned, the two polypeptides have approximately the specified percentage of identical amino acids. For example, "95% amino acid identity" refers to the comparison between the amino acids of two polypeptides, and when optimally aligned, 95% of the amino acids of the two polypeptides are identical.

In some embodiment, the wild-type DAAO is at least 65%, preferably at least 70%, 75% or 80%, more preferably at least 85%, 90% or 95%, and particularly 96%, 97%, 98% or 99% identical to one of SEQ ID NOs: 1-3.

In some embodiments, the modified DAAO of the present invention comprises 4, 5, 6, 7, 8, 9, 10, 11, 12, 13, 14, 15, 16, 17, 18, 19, 20 or more amino acid substitutions as compared to its wild-type, wherein the modified DAAO has the activity of catalyzing the oxidation of D-glufosinate into PPO. In some embodiments, the modified DAAO of the present invention comprises amino acid substitutions at positions 54, 56, 58 and 213, and the positions are numbered by reference to SEQ ID NO: 2. Preferably, the amino acid at position 54 is substituted by I, V, T or L, and more preferably I or V. Preferably, the amino acid at position 56 is substituted by N. Preferably, the amino acid at position 58 is substituted by H or Q, more preferably H. Preferably, the amino acid at position 213 is substituted by S or T, more preferably S. In some preferred embodiments, the modified DAAO comprises substitutions 54V, 56N, 58H and 213S, or substitution 54I, 56N, 58H and 213S as compared to its wild-type DAAO. In some embodiments, the modified DAAO further comprises amino acid substitution(s) at position(s) 210 and/or 221. Preferably, the amino acid at position 210 is substituted by A, G or P, more preferably A. Preferably, the amino acid at position 221 is substituted by R. Preferably, the modified DAAO of the present invention further comprises amino acid substitutions at one or more positions selected from the group consisting of 194, 237, 265, 273, 274, 300, 317 and 319. Preferably, the amino acid at position 194 is substituted by V or C, the amino acid at position 237 is substituted by V, the amino acid at position 265 is substituted by C, the amino acid at position 273 is substituted by D, the amino acid at position 274 is substituted by E, the amino acid at position 300 is substituted by S, the amino acid at position 317 is substituted by Y or W, the amino acid at position 319 is substituted by K. Preferably, the wild-type DAAO is at least 65%, preferably at least 70%, 75% or 80%, more preferably at least 85%, 90% or 95%, and particularly 96%, 97%, 98% or 99% identical to SEQ ID NO: 1.

In some embodiments, the modified DAAO comprises amino acid substitutions at positions 54, 58, 213 and 221, and the positions are numbered by reference to SEQ ID NO: 2. Preferably, the amino acid at position 54 is substituted by V, the amino acid at position 58 is substituted by Q, the amino acid at position 213 is substituted by S, and the amino acid at position 221 is substituted by R. In some embodiments, the modified DAAO further comprises amino acid substitution(s) at position(s) 210 and/or 56. Preferably, the amino acid at position 56 is substituted by N, and the amino acid at position 210 is substituted by A. Preferably, the modified DAAO of the present invention further comprises amino acid substitutions at one or more positions selected from the group consisting of 194, 237, 265, 273, 274, 300, 317 and 319, wherein the amino acid at position 194 is substituted by V or C, the amino acid at position 237 is substituted by V, the amino acid at position 265 is substituted by C, the amino acid at position 273 is substituted by D, the amino acid at position 274 is substituted by E, the amino acid at position 300 is substituted by S, the amino acid at position 317 is substituted by Y or W, and the amino acid at position 319 is substituted by K. Preferably, the wild-type DAAO is at least 65%, preferably at least 70%, 75% or 80%, more preferably at least 85%, 90% or 95%, and particularly 96%, 97%, 98% or 99% identical to SEQ ID NO: 1.

In some embodiments, the modified DAAO of the present invention comprises 4, 5, 6, 7, 8, 9, 10, 11, 12, 13, 14, 15, 16, 17, 18, 19, 20 or more amino acid substitutions as compared to its wild-type, wherein the modified DAAO has the activity of catalyzing the oxidation of D-glufosinate into PPO. In some embodiments, the modified DAAO of the present invention comprises amino acid substitutions at positions 54, 56, 58 and 213, and the positions are numbered by reference to SEQ ID NO: 2. Preferably, the amino acid at position 54 is substituted by I, V, T or L, and more preferably I or V. Preferably, the amino acid at position 56 is substituted by N. Preferably, the amino acid at position 58 is substituted by H or Q, more preferably H. Preferably, the amino acid at position 213 is substituted by S or T, more preferably S. In some preferred embodiments, the modified DAAO comprises substitutions 54V, 56N, 58H and 213S, or substitution 54I, 56N, 58H and 213S as compared to its wild-type DAAO. In some embodiments, the modified DAAO further comprises amino acid substitution(s) at position(s) 210 and/or 221. Preferably, the amino acid at position 210 is substituted by A, G or P, more preferably A. Preferably, the amino acid at position 221 is substituted by R. Preferably, the modified DAAO of the present invention further comprises amino acid substitutions at one or more positions selected from the group consisting of 2, 81, 97, 193, 300, 337 and 342, wherein the amino acid at position 2 is substituted by C or S, the amino acid at position 81 is substituted by Y, the amino acid at position 97 is substituted by V, the amino acid at position 193 is substituted by T, the amino acid at position 300 is substituted by T, the amino acid at position 337 is substituted by S, and the amino acid at position 342 is substituted by S or H. Preferably, the wild-type DAAO is at least 65%, preferably at least 70%, 75% or 80%, more preferably at least 85%, 90% or 95%, and particularly 96%, 97%, 98% or 99% identical to SEQ ID NO: 2.

In some embodiments, the modified DAAO comprises amino acid substitutions at positions 54, 58, 213 and 221, and the positions are numbered by reference to SEQ ID NO: 2. Preferably, the amino acid at position 54 is substituted by V, the amino acid at position 58 is substituted by Q, the amino acid at position 213 is substituted by S, and the amino acid at position 221 is substituted by R. In some embodiments, the modified DAAO further comprises amino acid substitution(s) at position(s) 210 and/or 56. Preferably, the amino acid at position 56 is substituted by N, and the amino acid at position 210 is substituted by A. Preferably, the modified DAAO of the present invention further comprises amino acid substitutions at one or more positions selected from the group consisting of 2, 81, 97, 193, 300, 337 and 342, wherein the amino acid at position 2 is substituted by C or S, the amino acid at position 81 is substituted by Y, the amino acid at position 97 is substituted by V, the amino acid at position 193 is substituted by T, the amino acid at position 300 is substituted by T, the amino acid at position 337 is substituted by S, and the amino acid at position 342 is substituted by S or H. Preferably, the wild-type DAAO is at least 65%, preferably at least 70%, 75% or 80%, more preferably at least 85%, 90% or 95%, and particularly 96%, 97%, 98% or 99% identical to SEQ ID NO: 2.

In some embodiments, the modified DAAO comprises 4-20, 4-15, 4-14, 4-13, 4-12, 4-11, 4-10, 4-9, 4-8, 4-7, 4-6 or 4-5 amino acid substitutions as compared to its wild-type. In some embodiments, the modified DAAO comprises 4, 5, 6, 7, 8, 9, 10, 11, 12, 13, 14, 15, 16, 17, 18, 19, 20 or more amino acid substitutions as compared to its wild-type as compared to its wild-type.

In some embodiments, the wild-type DAAO differs from one of SEQ ID NOs: 1-3 in comprising the substitution, deletion, insertion and/or addition of one or more amino acids. In some embodiments, the wild-type DAAO comprises conserved substitutions of one or more amino acids as compared to one of SEQ ID NOs: 1-3. In some embodiments, the wild-type DAAO comprises the insertion or deletion of one or more amino acids as compared to one of SEQ ID NOs: 1-3.

In some embodiments, the modified DAAO comprises 4, 5, 6, 7, 8, 9, 10, 11, 12, 13, 14, 15, 16, 17, 18, 19, 20 or more amino acid substitutions as compared to its wild-type as compared to its wild-type DAAO, wherein the modified DAAO has the activity of catalyzing the oxidation of D-glufosinate into PPO. In some embodiments, the modified DAAO comprises amino acid substitutions at positions 54, 56, 58 and 213, and the positions are numbered by reference to SEQ ID NO: 2, wherein the modified DAAO is at least 70%, 75%, 80%, 85%, 90%, 95%, 96%, 97% or 98% identical to one of SEQ ID NOs: 1-3. Preferably, the amino acid at position 54 is substituted by I, V, T or L, and more preferably I or V. Preferably, the amino acid at position 56 is substituted by N. Preferably, the amino acid at position 58 is substituted by H or Q, more preferably H. Preferably, the amino acid at position 213 is substituted by S or T, more preferably S. In some preferred embodiments, the modified DAAO polypeptide comprises a combination of substitutions 54V, 56N, 58H and 213S, or 54I, 56N, 58H and 213S as compared to its wild-type DAAO. In some embodiments, the modified DAAO further comprises amino acid substitution(s) at position(s) 210 and/or 221. Preferably, the amino acid at position 210 is substituted by A, G or P, more preferably A. Preferably, the amino acid at position 221 is substituted by R.

In some embodiments, the modified DAAO comprises amino acid substitutions at positions 54, 58, 213 and 221, and the positions are numbered by reference to SEQ ID NO: 2, wherein the modified DAAO is at least 70%, 75%, 80%, 85%, 90%, 95%, 96%, 97% or 98% identical to one of SEQ ID NOs: 1-3. Preferably, the amino acid at position 54 is substituted by V, the amino acid at position 58 is substituted by Q, the amino acid at position 213 is substituted by S, and the amino acid at position 221 is substituted by R. In some embodiments, the modified DAAO further comprises amino acid substitution(s) at position(s) 210 and/or 56. Preferably, the amino acid at position 56 is substituted by N, and the amino acid at position 210 is substituted by A.

In some embodiments, the modified DAAO of the present invention further comprises amino acid substitutions at one or more positions selected from the group consisting of 2, 81, 97, 193, 194, 237, 265, 273, 274, 300, 317, 319, 337 and 342, and the positions are numbered by reference to SEQ ID NO: 2, wherein the modified DAAO has the activity of catalyzing the oxidation of D-glufosinate into PPO. Preferably, the amino acid at position 2 is substituted by C or S, the amino acid at position 81 is substituted by Y, the amino acid at position 97 is substituted by V, the amino acid at position 193 is substituted by T, the amino acid at position 194 is substituted by V or C, the amino acid at position 237 is substituted by V, the amino acid at position 265 is substituted by C, the amino acid at position 273 is substituted by D, the amino acid at position 274 is substituted by E, the amino acid at position 300 is substituted by S or T, the amino acid at position 317 is substituted by Y or W, the amino acid at position 319 is substituted by K, the amino acid at position 337 is substituted by S, and the amino acid at position 342 is substituted by S or H.

Alternatively, in some embodiments, the modified DAAO of the present invention further comprises substitutions at one or more positions selected from the group consisting of 194, 237, 265, 273, 274, 300, 317 and 319, and the positions are numbered by reference to SEQ ID NO: 2, wherein the modified DAAO has the activity of catalyzing the oxidation of D-glufosinate into PPO. Preferably, the amino acid at position 194 is substituted by V or C, the amino acid at position 237 is substituted by V, the amino acid at position 265 is substituted by C, the amino acid at position 273 is substituted by D, the amino acid at position 274 is substituted by E, the amino acid at position 300 is substituted by S, the amino acid at position 317 is substituted by Y or W, and the amino acid at position 319 is substituted by K.

Alternatively, in some embodiments, the modified DAAO of the present invention further comprises substitutions at one or more positions selected from the group consisting of 2, 81, 97, 193, 300, 337 and 342, and the positions are numbered by reference to SEQ ID NO: 2, wherein the modified DAAO has the activity of catalyzing the oxidation of D-glufosinate into PPO. Preferably, the amino acid at position 2 is substituted by C or S, the amino acid at position 81 is substituted by Y, the amino acid at position 97 is substituted by V, the amino acid at position 193 is substituted by T, the amino acid at position 300 is substituted by T, the amino acid at position 337 is substituted by S, and the amino acid at position 342 is substituted by S or H.

In some embodiments, the modified DAAO comprises amino acid substitutions at positions 54, 58, 194 and 213 as compared to SEQ ID NO: 1, wherein the modified DAAO has the activity of catalyzing the oxidation of D-glufosinate into PPO, wherein the modified DAAO is at least 70%, 75%, 80%, 85%, 90%, 95%, 96%, 97% or 98% identical to SEQ ID NO: 1. Preferably, the amino acid at position 54 is substituted by I, V, T or L, the amino acid at position 58 is substituted by H or Q, the amino acid at position 194 is substituted by V or C, and the amino acid at position 213 is substituted by S or T. In some embodiments, the modified DAAO further comprises amino acid substitutions at one or more positions selected from the group consisting of positions 56, 210, 221, 237, 265, 273, 274, 300, 317 and 319. Preferably, the amino acid at position 56 is substituted by N, the amino acid at position 210 is substituted by A, G or P, the amino acid at position 221 is substituted by R, the amino acid at position 237 is substituted by V, the amino acid at position 265 is substituted by C, the amino acid at position 273 is substituted by D, the amino acid at position 274 is substituted by E, the amino acid at position 300 is substituted by S, the amino acid at position 317 is substituted by Y or W, and the amino acid at position 319 is substituted by K. In some embodiments, the modified DAAO of the present invention further comprises conserved substitutions of one or more amino acids, or comprises the insertion or deletion of one or more amino acids as compared to SEQ ID NO: 1.

The term "conserved substitution" is also referred to as substitution by "homologous" amino acid residue, meaning a substitution in which an amino acid is replaced by an amino acid residue with a similar side chain, e.g., amino acids with a basic side chain (e.g. lysine, arginine and histidine), amino acids with an acidic side chain (e.g. aspartic acid, glutamic acid), amino acids with a non-charged polar side chain (e.g. glycine, asparagine, glutamine, serine, threonine, tyrosine, cysteine), amino acids with a non-polar side chain (e.g. alanine, valine, leucine, isoleucine, proline, phenylalanine, methionine, tryptophan), amino acids with a beta-branched side chain (e.g. threonine, valine, isoleucine) and amino acids with an aromatic side chain (e.g. tyrosine, phenylalanine, tryptophan, histidine).

Generally, a conserved substitution of amino acids results in minimal influence to the activity of the obtained protein. Such substitutions are described below. A conserved substitution is to replace an amino acid with an amino acid that is similar in size, hydrophobicity, charge, polarity, spatial characteristics, and aromaticity. When it is desired to precisely regulate the properties of a protein, the substitutions are generally conserved.

As used herein, "homologous" amino acid residues refer to amino acid residues with similar chemical properties, which are related to hydrophobicity, charge, polarity, steric characteristics, aromatic characteristics, etc. Examples of amino acids that are homologous to each other include lysine, arginine, and histidine, which are positively charged; glutamic acid and aspartic acid, which are negatively charged; glycine, alanine, valine, leucine, isoleucine, proline, and phenylalanine, which are hydrophobic; serine, threonine, cysteine, methionine, tryptophan, tyrosine, asparagine, glutamine, which are polar; phenylalanine, tyrosine, and tryptophan, which are Aromatic; serine and threonine, or glutamine and asparagine, or leucine and isoleucine, which have chemically similar side chain groups.

Examples of conservative amino acid substitutions in proteins include: Ala is substituted by Ser, Arg is substituted by Lys, Asn is substituted by Gln or His, Asp is substituted by Glu, Cys is substituted by Ser, Gln is substituted by Asn, Glu is substituted by Asp, Gly is substituted by Pro, His is substituted by Asn or Gln, Ile is substituted by Leu Or Val, Leu is substituted by Ile or Val, Lys is substituted by Arg or Gln, Met is substituted by Leu or Ile, Phe is substituted by Met, Leu or Tyr, Ser is substituted by Thr, Thr is substituted by Ser, Trp is substituted by Tyr, Tyr is substituted by Trp or Phe, and Val is substituted by Ile or Leu.

In some embodiments, the modified DAAO comprises or consists of the amino acid sequence of one of SEQ ID NOs: 5-86, or the modified DAAO comprises an amino acid sequence comprising 1-10 amino acid substitutions at positions other than positions 54, 56, 58, 194, 210, 213, 221, 237, 265, 273, 274, 300, 317 and 319 as compared to one of SEQ ID NOs: 5-30 and 66-76, comprising 1-10 amino acid substitutions at positions other than positions 2, 54, 56, 58, 81, 97, 193, 210, 213, 221, 300, 337 and 342 as compared to one of SEQ ID NOs: 31-57 and 77-86, or comprising 1-10 amino acid substitutions at positions other than positions 54, 56, 58, 210, 213 and 221 as compared to one of SEQ ID NOs: 58-65, wherein the modified DAAO has the activity of catalyzing the oxidation of D-glufosinate into PPO. In some embodiments, the modified DAAO comprises or consists of the amino acid sequence of one of SEQ ID NOs: 5-86, or the modified DAAO comprises 1, 2, 3, 4, 5, 6, 7, 8, 9, 10 or more amino acid substitutions at positions other than positions 54, 56, 58, 194, 210, 213, 221, 237, 265, 273, 274, 300, 317 and 319 as compared to one of SEQ ID NOs: 5-30 and 66-76, comprises 1, 2, 3, 4, 5, 6, 7, 8, 9, 10 or more amino acid substitutions at positions other than positions 2, 54, 56, 58, 81, 97, 193, 210, 213, 221, 300, 337 and 342 as compared to one of SEQ ID NOs: 31-57 and 77-86, or comprises 1, 2, 3, 4, 5, 6, 7, 8, 9, 10 or more amino acid substitutions at positions other than positions 54, 56, 58, 210, 213 and 221 as compared to one of SEQ ID NOs: 58-65, and wherein the modified DAAO has the activity of catalyzing the oxidation of D-glufosinate into PPO. In some embodiments, the modified DAAO is at least 70%, 75%, 80%, 85%, 90%, 95%, 96%, 97%, 98% or 99% identical to one of SEQ ID NOs: 1-3.

As used herein, the activity of an enzyme refers to a decrease in the substrate or an increase in the product per unit time in a chemical reaction catalyzed by the enzyme in unit mass under certain conditions. For example, the activity of the modified DAAO of the present invention can be expressed by the amount of the decrease in D-glufosinate or the increase in PPO per unit time under the catalysis of unit mass of modified DAAO under certain conditions.

The activity of an enzyme herein can also refer to the relative activity of the enzyme, expressed as the ratio of the activity of the enzyme of interest to the activity of a given enzyme that catalyzes the same reaction, such as percentage relative activity.

In some embodiments, the activity of the modified DAAO of the present invention is expressed as the percentage relative activity as compared to SEQ ID NO: 4. In some embodiments, the activity of the modified DAAO on catalyzing the oxidation of D-glufosinate into PPO is at least 100%, 105%, 110%, 120%, 130%, 150%, 170%, 200%, 250%, 300% or more of the activity of SEQ ID NO: 4 on catalyzing the oxidation of D-glufosinate into PPO.

It is also beneficial for the industrial production to improve the stability of the modified DAAO. In some embodiments, the stability is thermal stability, which refers to the ability of the enzyme to maintain activity after incubating at a certain temperature (such as 40-60° C. or higher) for a certain time (such as 10 minutes to 1 hour). In some embodiments, the modified DAAO has better thermal stability than the polypeptide of SEQ ID NO: 4. For example, after an incubation at 43-45° C. for 20 minutes, the activity of the modified DAAO of the present invention is at least 100%, 105%, 110%, 120%, 130%, 150%, 170%, 200%, 250%, 300% or higher of the activity of the polypeptide of SEQ ID NO: 4. Alternatively, the modified DAAO of the present invention has a higher T50, where T50 refers to the temperature at which the enzyme activity decreases by 50% after an incubation for one hour. In some embodiments, the T50 of the modified DAAO of the present invention is about 1, 2, 3, 4, 5, 6, 7, 8, 9, 10° C. or more higher than the polypeptide of SEQ ID NO: 4.

In some embodiments, the modified DAAO has better thermal stability than the polypeptide of SEQ ID NO: 4, and the activity thereof on catalyzing the oxidation of D-glufosinate into PPO is at least 100%, 105%, 110%, 120%, 130%, 150%, 170%, 200%, 250%, 300% or more of the activity of SEQ ID NO: 4 on catalyzing the oxidation of D-glufosinate into PPO.

II. The Polynucleotide Encoding the Modified DAAO

As used herein, the term "polynucleotide" or "nucleic acid molecule" includes DNA molecules (e.g. cDNA or genomic DNA) and RNA molecules (e.g. mRNA) and analogs of DNA or RNA produced using nucleotide analogs. The nucleic acid molecule may be single-stranded or double-stranded, preferably double-stranded DNA. The synthesis of the nucleic acid can use nucleotide analogs or derivatives (for example, inosine or phosphorothioate nucleotides). Such nucleotides can be used, for example, to prepare nucleic acids with altered base pairing ability or increased nuclease resistance.

The present invention also provides a polynucleotide encoding the modified DAAO of the present invention. Therefore, in the present invention, the term modification also includes genetic manipulation of the polynucleotide encoding the DAAO polypeptide of the present invention. The modification can be substitution, deletion, insertion and/or addition of nucleotides.

As used herein, the term "encoding" means that a polynucleotide directly specifies the amino acid sequence of its protein product. The boundaries of the coding sequence are generally determined by an open reading frame, which generally starts with the ATG start codon or other start codons such as GTG and TTG, and ends with a stop codon such as TAA, TAG and TGA. The coding sequence can be a DNA, cDNA or recombinant nucleotide sequence.

In addition, nucleic acid molecules covering all or part of the nucleic acid sequence of the present invention can be isolated by polymerase chain reaction (PCR), using oligonucleotide primers which are designed and synthesized based on the sequence information comprised in the sequence.

The polynucleotide of the present invention can be amplified with cDNA, mRNA or genomic DNA as the template and suitable oligonucleotide primers according to standard PCR amplification techniques. The nucleic acid amplified as above can be cloned into a suitable vector and characterized by DNA sequence analysis.

The polynucleotide of the present invention can be prepared by standard synthesis techniques, for example, by using an automated DNA synthesizer.

The present invention also relates to the complementary strand of the nucleic acid molecule described herein. A nucleic acid molecule that is complementary to other nucleotide sequence is a molecule that is sufficiently complementary to the nucleotide sequence so that it can hybridize with the other nucleotide sequences to form a stable duplex.

As used herein, the term "hybridization" that nucleotides sequences, which are at least about 90%, preferably at least about 95%, more preferably at least about 96%, and more preferably at least 98% homologous to each other, generally maintain hybridization with each other under given stringent hybridization and washing conditions.

A person skilled in the art knows various conditions for hybridization, such as stringent hybridization conditions and highly stringent hybridization conditions. See, for example, Sambrook et al., 1989, Molecular Cloning, A Laboratory Manual, Cold Spring Harbor Press, N.Y.; and Ausubel et al. (eds.), 1995, Current Protocols in Molecular Biology, John Wiley & Sons, N.Y.

Of course, the polynucleotide of the present invention does not include a polynucleotide that only hybridizes to a poly A sequence (such as the 3' end poly(A) of mRNA) or a complementary stretch of poly T (or U) residues.

III. The Expression and Production of the Modified DAAO

In order to express the modified DAAO of the present invention, also provided is a nucleic acid construct and a vector comprising the polynucleotide of the present invention, such as an expression vector.

As used herein, the term "expression" includes any step involved in the production of a polypeptide, including but not limited to transcription, post-transcriptional modification, translation, post-translational modification, and secretion.

The term "nucleic acid construct" refers to a single-stranded or double-stranded nucleic acid molecule, which is isolated from a naturally occurring gene or modified to contain a nucleic acid segment that does not naturally occur. When the nucleic acid construct contains the control sequences required to express the coding sequence of the present invention, the term nucleic acid construct is synonymous with the term "expression cassette".

The term "expression vector" refers herein to a linear or circular DNA molecule comprising a polynucleotide encoding the polypeptide of the present invention operably linked to additional nucleotides provided for the expression of the polynucleotide, for example, control sequence. The expression vector includes a viral vector or a plasmid vector.

The term "control sequence" herein includes all elements necessary or beneficial for the expression of the polynucleotide encoding the polypeptide of the present invention. Each control sequence may be natural or foreign to the nucleotide sequence encoding the polypeptide, or natural or foreign to each other. Such control sequences include, but are not limited to, leader sequence, polyadenylation sequence, propeptide sequence, promoter, signal peptide sequence, and transcription terminator. At a minimum, control sequences include a promoter and signals for the termination of transcription and translation.

For example, the control sequence may be a suitable promoter sequence, a nucleotide sequence recognized by the host cell to express the polynucleotide encoding the polypeptide of the present invention. The promoter sequence contains a transcription control sequence that mediates the expression of the polypeptide. The promoter may be any nucleotide sequence that exhibits transcriptional activity in the selected host cell, for example, lac operon of *E. coli*. The promoters also include mutant, truncated and hybrid promoters, and can be obtained from genes encoding extracellular or intracellular polypeptides, which are homologous or heterologous to the host cell.

The term "operably linked" herein refers to a configuration in which a control sequence is placed at an appropriate position relative to the coding sequence of the polynucleotide sequence, whereby the control sequence directs the expression of the polypeptide coding sequence.

The polynucleotide encoding the polypeptide of the present invention can be subjected to various manipulations to allow the expression of the polypeptide. Before the insertion thereof into a vector, manipulation of the polynucleotide according to the expression vector is desirable or necessary. Techniques for modifying polynucleotide sequences with recombinant DNA methods are well known in the art.

In order to identify and select host cells comprising the expression vector of the present invention, the vector of the present invention preferably contains one or more selectable markers, which allow simple selection of transformed, transfected, transduced, etc. cells. A selectable marker is a gene, of which the product provides biocide or virus resistance, heavy metal resistance, supplemental auxotrophs, etc. For example, the bacterial selectable marker is the dal gene from *Bacillus subtilis* or *Bacillus licheniformis*, or a marker that confers antibiotic resistance such as ampicillin, kanamycin, chloramphenicol or tetracycline resistance.

The vector of the present invention can be integrated into the genome of the host cell or autonomously replicate in the cell, which is independent of the genome. The elements required for the integration into the genome of the host cell or the autonomous replication are known in the art (see, for example, the aforementioned Sambrook et al., 1989).

Vector DNA can be introduced into prokaryotic or eukaryotic cells by conventional transformation or transfection techniques. As used herein, the terms "transformation" and "transfection" refer to various techniques for introducing foreign nucleic acids (such as DNA) into host cells, which are well known in the art, and can be found in, for example, the aforementioned Sambrook et al., 1989; Davis et al., Basic Methods in Molecular Biology (1986) and other laboratory manuals.

The present invention also relates to a recombinant host cell comprising the polynucleotide of the present invention, which is advantageously used in the recombinant production of DAAO polypeptides. The vector comprising the polynucleotide of the present invention is introduced into the host cell, whereby the vector is retained as a chromosomal integrant or as a self-replicating extrachromosomal vector. A person skilled in the art knows the conventional vectors and host cells for expressing proteins.

In some embodiments, the host cell of the present invention is an *E. coli* cell, such as *E. coli* BL21 (DE3). In some embodiments, the expression vector is pET-30a(+).

The modified DAAO of the present invention can be operably linked to a non-DAAO polypeptide (for example, a heterologous amino acid sequence) to form a fusion protein. For example, in one embodiment, the fusion protein is a GST-DAAO fusion protein, wherein the DAAO sequence is fused to the C-terminus of the GST sequence. This fusion protein can facilitate the purification of recombinant DAAO. In another embodiment, the fusion protein is a DAAO protein containing a heterologous signal sequence at its N-terminus. In certain host cells (e.g., mammalian and yeast host cells), the expression and/or secretion of DAAO can be increased by the use of a heterologous signal sequence.

IV. The Production of L-Glufosinate

Moreover, the present invention provides a method for preparing L-glufosinate comprising contacting the modified DAAO or the host cell of the present invention with D-glufosinate.

In some embodiments, the method for preparing L-glufosinate-ammonium of the present invention comprises the steps of:

(a) providing the activity of the modified DAAO of the present invention and D-glufosinate to the reaction medium, and optionally, providing catalase activity to the reaction medium, (b) incubating the reaction medium to oxidize D-glufosinate into PPO, and (c) producing L-glufosinate by the reduction or transamination of PPO.

In some embodiments, a cell-free-catalysis method is used to produce L-glufosinate, and the modified DAAO of the present invention is provided in step (a). In some embodiments, the modified DAAO of the invention which is free or immobilized can be used. Catalase can also be immobilized.

In some embodiments, the incubation is performed at 20-50° C., preferably 25-40° C., more preferably 28-35° C., e.g., 30° C.

In some embodiments, the medium is a buffer, such as PBS, and Tris-HCl buffer. In one embodiment, the medium is a Tris-HCl buffer, such as a Tris-HCl buffer of 50 mM, pH 8.0.

In some embodiments, the reaction medium is a medium partially or entirely composed of cell culture medium, and the activity of the modified DAAO of the present invention is provided by the host cell of the present invention, which is cultured in the reaction medium.

In some embodiments, the reaction medium is a medium partially or entirely composed of cell culture medium, and the catalase activity is provided by the host cell of the present invention or by a second host cell, which is Culture in the reaction medium.

In some embodiments, the host cell of the present invention and/or the second host cell are cultured and expanded in a cell culture medium, and then, the expanded host cells are separated from the cell culture medium, and a buffer or water is used to resuspend the biomass. D-Glufosinate is added to the buffer or water before, during or after the addition of the expanded host cells.

In some embodiments, bacterial cells can be used, such as *E. coli* cells.

EXAMPLES

A person skilled in the art will understand the present invention more clearly through the following examples. It should be understood that the examples are for illustration only, rather than limiting the scope of the present invention Example 1. Materials and Methods Unless otherwise specified, the experimental methods used in the present invention are all conventional methods. The particular gene cloning operation can be seen in the aforementioned Sambrook et al., 1989.

i) Reagents:

DNA polymerase (Prime STAR Max DNA Polymerase) and DpnI endonuclease were purchased from TaKaRa; plasmid isolation kit was purchased from Axygen; catalase was purchased from Zaozhuang Quanding Biological Technology Co., Ltd., item number QD-001; and D,L-Glufosinate was purchased from Lier Chemical Co., Ltd.

ii) Vectors and Strains:

The expression vector used was pET-30a(+), the plasmid was purchased from Novagen; and the host cell used was *E. coli* BL21(DE3), purchased from Tiangen BioTech (Beijing) Co., Ltd.

iii) Sequencing and Primer Synthesis were Accomplished by Synbio Technologies Co., Ltd.

iv) Site-Directed Mutation:

Specific primer pairs were designed to introduce the desired substitutions at the bases corresponding to the amino acid positions that are needed to be mutated. The isolated pre-mutation plasmid (comprising the coding sequence for the wild-type DAAO, and pET-30a(+) backbone) was used as the template, and mutations were introduced by PCR using Quickchange technology (Nucleic Acids Research, 2004, 32(14):e115). After PCR amplification, the amplified product was digested with DpnI for 4 h to remove the template plasmid. The digested product was transformed into E. coli BL21(DE3) competent cells, followed by spreading the cells on LB agar (containing 50 mg/L kanamycin), picking single colonies into LB broth (containing 50 mg/L kanamycin) for culture, and sequencing to verify the correct mutants. The verified clone is stored at −80° C. for future use.

v) Protein Expression and the Preparation of Crude Enzyme Solution:

The stored clones were activated on LB agar. Then, single colonies were inoculated into LB broth (containing 50 mg/L kanamycin), and incubated at 37° C. with shaking for 12 h. 1 mL culture was transferred to 50 mL fresh LB broth (containing 50 mg/L kanamycin), incubated with shaking at 37° C. until OD600 reaches about 0.6, and incubated at 25° C. for 16 h to induce protein expression after the addition of IPTG (final concentration of 0.4 mM).

After the incubation, the culture was centrifuged at 4,000 g for 10 min at 4° C., the supernatant was discarded, and E. coli cells were collected. The collected E. coli cells were resuspended in 15 mL pre-chilled phosphate buffered saline (PBS), pH 7.0, and were sonicated at 4° C. The cell disruption solution was centrifuged at 6,000 g at 4° C. for 15 min to remove the precipitate, and the supernatant obtained was the crude enzyme solution containing the recombinant enzyme (13 g/L).

vi) Determination of the Enzyme Activity

D,L-Glufosinate was dissolved in 50 mM Tris-HCl buffer, pH=8, and the final concentration of D,L-Glufosinate in the solution was 100 mM. 2 g/L crude enzyme and 2 g/L catalase were added to the above solution, which was then continuously shaked (400 rpm) at 30° C. on a shaker for 2 hours. The decrease of D-glufosinate and the ee value were detected by sampling and detecting with OPA pre-column derivatization high performance liquid chromatography to determine the initial rate of the catalyzed reaction.

Example 2. The Preparation and Detection of the Mutants of the DAAO from *Rhodotorula toruloides* (RtDAAO)

The mutants were prepared according to the method of Example 1, using the nucleic acid encoding RtDAAO (SEQ ID NO: 1) as the template. The resulting mutants are shown in Table 1, in which the mutant of SEQ ID NO: 4 is the mutant reported in U.S. Pat. No. 9,834,802 (RtDAAO N54V, F58Q, M213S). The resulting mutants were incubated at 45° C. for 20 minutes and the enzyme activity was measured according to the method described in Example 1. The results are shown in Table 1, where the relative enzyme activity refers to (after incubation) the percentage of the activity of the mutant vs. the activity of SEQ ID NO: 4 (100-150% is expressed as "+", 150-200% is expressed as "++", and more than 200% is expressed as "+++").

TABLE 1

| Mutations in the mutants | SEQ ID NO: | Relative enzyme activity |
|---|---|---|
| N54V, F58Q, A194V, M213S | 5 | +++ |
| N54V, F58Q, A194C, M213S | 6 | +++ |
| N54V, F58Q, M213S, E273D | 7 | ++ |
| N54V, F58Q, M213S, A317Y | 8 | ++ |
| N54V, F58Q, M213S, A317W | 9 | +++ |
| N54V, F58Q, M213S, G274E | 10 | ++ |
| N54V, F58Q, M213S, A319K | 11 | + |
| N54V, F58Q, A194C, M213S, A317Y | 12 | +++ |

Then, further mutations were introduced on the basis of SEQ ID NO: 12, and the resulting mutants are shown in Table 2. The relative enzyme activities of the mutants were measured (the percentage of the activity of the mutant vs. the activity of SEQ ID NO: 4, without heat treatment). Then, the resulting mutant was incubated at a series of temperatures (40-60° C.) for 1 h, and T50 was measured (the enzyme activity was reduced by 50% after incubating at the temperature for 1 h). The results are shown in Table 2.

TABLE 2

| Mutations in the mutants | SEQ ID NO: | T50* | Relative enzyme activity |
|---|---|---|---|
| N54V, F58Q, M213S | 4 | 41-43° C. | 100% |
| N54V, F58Q, A194C, M213S, A317Y | 12 | 47-48° C. | 103% |
| N54V, F58Q, A194C, M213S, T265C, A317Y | 13 | 49-50° C. | 124% |
| N54V, F58Q, A194C, M213S, T265C, V300S, A317Y | 14 | 52-53° C. | 128% |

Amino acid substitutions were further introduced on the basis of SEQ ID NO: 14, and the enzyme activities of the mutants were tested (without heat treatment). The results are shown in Table 3. The relative enzyme activity refers to the percentage of the activity of the mutant vs. the activity of SEQ ID NO: 4, without heat treatment (110-120% is expressed as "+", 120-150% is expressed as "++", 150-200% is expressed as "+++", and greater than 200% is expressed as "++++").

TABLE 3

| Mutations in the mutants | SEQ ID NO: | Relative enzyme activity |
|---|---|---|
| N54V, F58Q, A194C, M213T, T265C, V300S, A317Y | 15 | ++ |
| N54V, F58Q, A194C, M213S, R210G, T265C, V300S, A317Y | 16 | ++ |
| N54V, F58Q, A194C, M213S, R210P, T265C, V300S, A317Y | 17 | ++ |
| N54V, F58Q, A194C, M213S, R210A, T265C, V300S, A317Y | 18 | ++ |
| N54V, F58Q, A194C, M213S, P221R, T265C, V300S, A317Y | 19 | +++ |
| N54V, F58Q, A194C, M213S, T237A, T265C, V300S, A317Y | 20 | ++ |
| N54V, F58Q, A194C, M213S, T237V, T265C, V300S, A317Y | 21 | ++ |
| N54V, T56N, F58Q, A194C, M213S, T265C, V300S, A317Y | 22 | +++ |
| N54T, T56N, F58Q, A194C, M213S, T265C, V300S, A317Y | 23 | +++ |

TABLE 3-continued

| Mutations in the mutants | SEQ ID NO: | Relative enzyme activity |
|---|---|---|
| N54I, T56N, F58Q, A194C, M213S, T265C, V300S, A317Y | 24 | ++++ |
| N54V, T56N, F58H, A194C, M213S, T265C, V300S, A317Y | 25 | ++++ |
| N54L, T56N, F58Q, A194C, M213S, T265C, V300S, A317Y | 26 | ++++ |
| N54I, T56N, F58H, A194C, M213S, T265C, V300S, A317Y | 27 | ++++ |
| N54V, T56N, F58H, A194C, M213S, T237V, T265C, V300S, A317Y | 28 | ++++ |
| N54V, T56N, F58H, A194C, M213S, R210A, T237V, T265C, V300S, A317Y | 29 | ++++ |
| N54I, T56N, F58H, A194C, M213S, R210A, P221R, T265C, V300S, A317Y | 30 | ++++ |

Example 3. The Preparation and Detection of the Mutants of the DAAO from *Rhodotorula* sp. JG-1b (RsDAAO)

The mutants were prepared according to the method of Example 1, using the nucleic acid encoding RsDAAO (SEQ ID NO: 2) as the template, and the enzyme activity was measured. The resulting mutants and enzyme activities thereof are shown in Table 4, wherein the relative enzyme activity refers to the percentage of the activity of the mutant vs. the activity of SEQ ID NO: 4, without heat treatment (less than 70% is expressed as "−−", 70-100% is expressed as "−", 110-120% is expressed as "+", 120-150% is expressed as "++", 150-200% is expressed as "+++", more than 200% is expressed as "++++"), and the activity of wild-type RsDAAO (SEQ ID NO: 2) is 0.

TABLE 4

| Mutations in the mutants | SEQ ID NO: | Relative enzyme activity |
|---|---|---|
| N54L, T56N, F58Q | 31 | −− |
| N54T, T56N, F58Q | 32 | −− |
| N54I, T56N, F58H | 33 | +++ |
| N54V, T56N, F58H | 34 | ++ |
| N54L, T56N, F58Q, M213S | 35 | +++ |
| N54T, T56N, F58Q, M213S | 36 | +++ |
| N54I, T56N, F58H, M213S | 37 | ++++ |
| N54V, T56N, F58H, M213S | 38 | ++++ |

On the basis of SEQ ID NO: 38, amino acid substitutions were further introduced, and the enzyme activities of the resulting mutant were measured. The resulting mutants are shown in Table 5. The activities of the mutants (without heat treatment) are equivalent to SEQ ID NO: 38. The mutant of SEQ ID NO: 38 and the mutant obtained by further introducing amino acid substitutions were incubated at 43° C. for 20 min, and the activities of the incubated mutants were measured. The results are shown in Table 5, where the relative enzyme activity refers to (after 20 minutes of incubation at 43° C.) the percentage of the activity of the mutant vs. the activity of SEQ ID NO: 38 (150-200% is expressed as "++", and more than 200% is expressed as "+++").

TABLE 5

| Mutations in the mutants | SEQ ID NO: | Relative enzyme activity |
|---|---|---|
| T2C, N54V, T56N, F58H, M213S | 39 | +++ |
| T2S, N54V, T56N, F58H, M213S | 40 | ++ |
| N54V, T56N, F58H, F81Y, M213S | 41 | ++ |
| N54V, T56N, F58H, A97V, M213S | 42 | +++ |
| N54V, T56N, F58H, E193T, M213S | 43 | ++ |
| N54V, T56N, F58H, M213S, S300T | 44 | +++ |
| N54V, T56N, F58H, M213S, A337S | 45 | +++ |
| N54V, T56N, F58H, M213S, G342S | 46 | +++ |
| T2S, N54V, T56N, F58H, F81Y, A97V, E193T, M213S, A337S | 47 | +++ |
| N54V, T56N, F58H, A97V, E193A, M213S, A337S, G342H | 48 | +++ |
| T2C, N54V, T56N, F58H, F81Y, A97V, M213S, A337S | 49 | +++ |
| T2C, N54V, T56N, F58H, F81Y, A97V, E193A, M213S, G342S | 50 | +++ |
| N54V, T56N, F58H, A97V, E193T, M213S, A337S, G342H | 51 | +++ |
| N54V, T56N, F58H, F81Y, A97V, E193T, M213S, A337S, G342H | 52 | +++ |
| N54V, T56N, F58H, A97V, E193T, M213S, S300T, A337S, G342H | 53 | +++ |
| N54V, T56N, F58H, F81Y, A97V, E193T, M213S, S300T, A337S, G342H | 54 | +++ |

On the basis of SEQ ID NO: 54, amino acid substitutions were further introduced, and the enzyme activities of the resulting mutants were measured. The resulting mutants and the enzyme activities thereof are shown in Table 6, where the relative enzyme activity refers to (without heat treatment) the percentage of the activity of the mutant vs. the activity of SEQ ID NO: 4 (120-150% is expressed as "++", 150-200% is expressed as "+++", more than 200% is expressed as "++++").

TABLE 6

| Mutations in the mutants | SEQ ID NO: | Relative enzyme activity |
|---|---|---|
| N54V, T56N, F58H, A97V, E193T, R210A, M213S, S300T, A337S, G342H | 55 | ++++ |
| N54V, T56N, F58H, A97V, E193T, M213S, P221R, S300T, A337S, G342H | 56 | ++++ |
| N54V, T56N, F58H, A97V, E193T, R210A, M213S, P221R, S300T, A337S, G342H | 57 | ++++ |

Example 4. The Preparation and Detection of the Mutants of the DAAO from *Rhodotorula taiwanensis* (RtnDAAO)

The mutants were prepared according to the method of Example 1, using the nucleic acid encoding RtnDAAO (SEQ ID NO: 3) as the template, and the enzyme activity was measured. The resulting mutants and the enzyme activities thereof are shown in Table 7, wherein the relative enzyme activity refers to the percentage of the activity of the mutant vs. the activity of SEQ ID NO: 4 (less than 70% is expressed as "−−", 70-100% is expressed as "−", 110-120% is expressed as "+", 120-150% is expressed as "++"), and the activity of wild-type RtnDAAO (SEQ ID NO: 3) is 0.

TABLE 7

| Mutations in the mutants | SEQ ID NO: | Relative enzyme activity |
|---|---|---|
| F58K, M213T | 58 | -- |
| N54L, T56N, F58Q, M213S | 59 | -- |
| N54T, T56N, F58Q, M213S | 60 | -- |
| N54I, T56N, F58H, M213S | 61 | – |
| N54V, T56N, F58H, M213S | 62 | + |
| N54V, T56N, F58H, R210A, M213S | 63 | ++ |
| N54V, T56N, F58H, M213S, P221R | 64 | ++ |
| N54V, T56N, F58H, R210A, M213S, P221R | 65 | ++ |

Example 5: Preparation of Mutants with Various Combinations of Substitutions Based on Different Wild-Types According to the method described in the above Examples, mutants were prepared by introducing various combinations of mutations into wild-type RtDAAO and RsDAAO, and the enzyme activities were measured.

The mutants based on RtDAAO and the enzyme activities thereof are shown in Table 8, wherein the relative enzyme activity refers to the percentage of the activity of the mutant vs. the activity of SEQ ID NO: 4 (110-120% is expressed as "+", 120-150% is expressed as "++", 150-200% is expressed as "+++", and greater than 200% is expressed as "++++").

TABLE 8

| Mutations in the mutants | SEQ ID NO: | Relative enzyme activity |
|---|---|---|
| N54V, F58Q, M213S | 4 | |
| N54I, T56N, F58H, M213S | 66 | ++++ |
| N54V, T56N, F58H, M213S | 67 | ++++ |
| N54V, F58Q, R210A, M213S | 68 | + |
| N54V, F58Q, M213S, P221R | 69 | ++++ |
| N54V, F58Q, R210A, M213S, P221R | 70 | ++++ |
| N54V, T56N, F58H, R210A, M213S | 71 | ++++ |
| N54V, T56N, F58H, M213S, P221R | 72 | ++++ |
| N54V, T56N, F58H, R210A, M213S, P221R | 73 | +++ |
| N54I, T56N, F58H, R210A, M213S | 74 | ++++ |
| N54I, T56N, F58H, M213S, P221R | 75 | ++ |
| N54I, T56N, F58H, R210A, M213S, P221R | 76 | ++++ |

The mutants based on RsDAAO and the enzyme activities thereof are shown in Table 9, where the relative enzyme activity refers to the percentage of the activity of the mutant vs. the activity of SEQ ID NO: 77 (110-120% is expressed as "+", 120-150% is expressed as "++", 150-200% is expressed as "+++", and greater than 200% is expressed as "++++").

TABLE 9

| Mutations in the mutants | SEQ ID NO: | Relative enzyme activity |
|---|---|---|
| N54V, F58Q, M213S | 77 | |
| N54I, T56N, F58H, M213S | 37 | ++++ |
| N54V, T56N, F58H, M213S | 38 | ++++ |
| N54V, F58Q, R210A, M213S | 78 | + |
| N54V, F58Q, M213S, P221R | 79 | +++ |
| N54V, F58Q, R210A, M213S, P221R | 80 | ++++ |
| N54V, T56N, F58H, R210A, M213S | 81 | ++++ |
| N54V, T56N, F58H, M213S, P221R | 82 | ++++ |
| N54V, T56N, F58H, R210A, M213S, P221R | 83 | +++ |
| N54I, T56N, F58H, R210A, M213S | 84 | ++++ |
| N54I, T56N, F58H, M213S, P221R | 85 | +++ |
| N54I, T56N, F58H, R210A, M213S, P221R | 86 | ++ |

We claim:

1. A modified D-amino acid oxidase (DAAO) comprising amino acid substitutions at positions 54, 56, 58 and 213 and further comprising amino acid substitution(s) at position(s) 210 and/or 221 as compared to its wild-type DAAO, wherein the positions are numbered by reference to SEQ ID NO: 2, wherein the amino acid at position 54 is substituted by I, V, T or L, the amino acid at position 56 is substituted by N, the amino acid at position 58 is substituted by H or Q, and the amino acid at position 213 is substituted by S or T, the amino acid at position 210 is substituted by A, G or P, and the amino acid at position 221 is substituted by R, and wherein the modified DAAO has the activity of catalyzing the oxidation of D-glufosinate into 2-carbonyl-4-(hydroxymethylphosphono)butyric acid (PPO).

2. The modified DAAO of claim 1, wherein the amino acid at position 54 is substituted by I or V, the amino acid at position 58 is substituted by H, and the amino acid at position 213 is substituted by S.

3. The modified DAAO of claim 1, wherein the amino acid at position 210 is substituted by A.

4. The modified DAAO of claim 1, wherein the modified DAAO further comprises amino acid substitutions at one or more positions selected from the group consisting of 2, 81, 97, 193, 194, 237, 265, 273, 274, 300, 317, 319, 337 and 342, wherein the amino acid at position 2 is substituted by C or S, the amino acid at position 81 is substituted by Y, the amino acid at position 97 is substituted by V, the amino acid at position 193 is substituted by T, the amino acid at position 194 is substituted by V or C, the amino acid at position 237 is substituted by V, the amino acid at position 265 is substituted by C, the amino acid at position 273 is substituted by D, the amino acid at position 274 is substituted by E, the amino acid at position 300 is substituted by S or T, the amino acid at position 317 is substituted by Y or W, the amino acid at position 319 is substituted by K, the amino acid at position 337 is substituted by S, and the amino acid at position 342 is substituted by S or H.

5. The modified DAAO of claim 1, wherein the modified DAAO further comprises amino acid substitutions at one or more positions selected from the group consisting of 194, 237, 265, 273, 274, 300, 317 and 319, wherein the amino acid at position 194 is substituted by V or C, the amino acid at position 237 is substituted by V, the amino acid at position 265 is substituted by C, the amino acid at position 273 is substituted by D, the amino acid at position 274 is substituted by E, the amino acid at position 300 is substituted by S, the amino acid at position 317 is substituted by Y or W, and the amino acid at position 319 is substituted by K.

6. The modified DAAO of claim 1, wherein the modified DAAO further comprises amino acid substitutions at one or more positions selected from the group consisting of 2, 81, 97, 193, 300, 337 and 342, wherein the amino acid at position 2 is substituted by C or S, the amino acid at position 81 is substituted by Y, the amino acid at position 97 is substituted by V, the amino acid at position 193 is substituted by T, the amino acid at position 300 is substituted by T, the amino acid at position 337 is substituted by S, and the amino acid at position 342 is substituted by S or H.

7. The modified DAAO of claim 1, comprising or consisting of
   (i) the amino acid sequence of one of SEQ ID NOs: 22-30, 35-57, 59-67, 71-76 and 81-86, or
   (ii) an amino acid sequence which is at least 90%, 95%, 96%, 97%, 98% or 99% identical to one of SEQ ID NOs: 1-3,
wherein the modified DAAO has the activity of catalyzing the oxidation of D-glufosinate into PPO.

8. A polynucleotide encoding the modified DAAO of claim 1.

9. An expressing vector comprising the polynucleotide of claim 8.

10. A host cell comprising the polynucleotide of claim 8.

11. A method of producing L-glufosinate, comprising the step of contacting the modified DAAO of claim 1 with D-glufosinate.

* * * * *